United States Patent
Pouzet et al.

(10) Patent No.: US 6,855,713 B2
(45) Date of Patent: *Feb. 15, 2005

(54) BENZIMIDAZOLE DERIVATIVES, A PROCESS FOR THEIR MANUFACTURE AND USE AS A MEDICINE

(75) Inventors: Pascale Pouzet, Biberach (DE); Christoph Hoenke, Ingelheim (DE); Claudia Heine, Biberach (DE); Ralf Anderskewitz, Laupheim (DE); Horst Dollinger, Schemmerhofen (DE); Herbert Nar, Ochsenhausen (DE); Hans Michael Jennewein, Wiesbaden (DE); Bernd Disse, Mainz (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 68 days.

This patent is subject to a terminal disclaimer.

(21) Appl. No.: 10/237,365

(22) Filed: Sep. 9, 2002

(65) Prior Publication Data

US 2003/0130265 A1 Jul. 10, 2003

Related U.S. Application Data

(60) Provisional application No. 60/332,978, filed on Nov. 14, 2001.

(30) Foreign Application Priority Data

Sep. 8, 2001 (DE) .......................... 101 44 658

(51) Int. Cl.[7] .................. A61K 31/497; C07D 403/12; C07D 401/12; A61P 37/00
(52) U.S. Cl. .................. 514/252.16; 514/322; 544/370; 546/199
(58) Field of Search .................. 544/370; 546/199; 514/322, 252.16

(56) References Cited

U.S. PATENT DOCUMENTS

| | | |
|---|---|---|
| 6,087,380 A | 7/2000 | Hauel et al. |
| 6,365,584 B1 | 4/2002 | Anderskewitz et al. |
| 6,407,130 B1 | 6/2002 | Anderskewitz et al. |
| 6,413,990 B1 | 7/2002 | Anderskewitz et al. |
| 6,512,000 B1 * | 1/2003 | Anderskewitz et al. ..... 514/396 |

FOREIGN PATENT DOCUMENTS

| | | |
|---|---|---|
| WO | WO 01/14342 A1 | 3/2001 |
| WO | WO 01/34572 A2 | 5/2001 |
| WO | WO 02/062785 A1 | 8/2002 |

OTHER PUBLICATIONS

Anderskewitz, R. et ali; "Aminocarbonyl–substituted Benzimidazoles Having Tryptase–Inhibitory Activity"; USSN 09/634,958; filed Aug. 8, 2000.

* cited by examiner

Primary Examiner—R Desai
Assistant Examiner—Robert Shiao
(74) Attorney, Agent, or Firm—Robert Raymond; Michael Morris; Philip I. Datlow

(57) ABSTRACT

The invention concerns benzimidazole derivatives of the general formula (I)

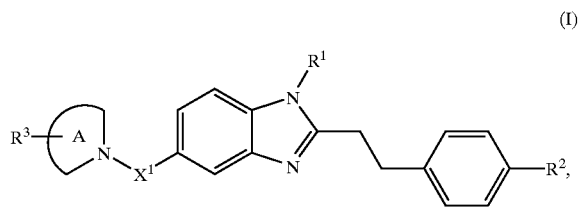

(I)

in which the radicals $R^1$, $R^2$, $R^3$, $X^1$ and A can have the meanings assigned to them in the specification, their prodrugs, processes for their production as well as the use of the benzimidazole derivatives as medicines, especially as medicines that have trypsin-inhibiting action.

14 Claims, No Drawings

BENZIMIDAZOLE DERIVATIVES, A PROCESS FOR THEIR MANUFACTURE AND USE AS A MEDICINE

RELATED APPLICATIONS

Benefit of U.S. Provisional Application Ser. No. 60/332,978, filed on Nov. 14, 2001 is hereby claimed, and said provisional application is herein incorporated by reference in its entirety.

FIELD OF THE INVENTION

The present invention relates to benzimidazole derivatives of the formula (I)

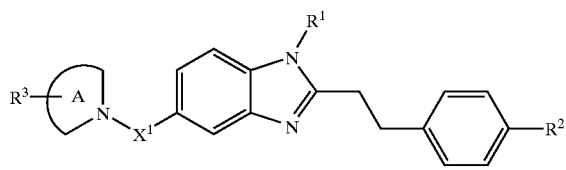

(I)

in which the residues $X^1$, $R^1$, $R^2$, $R^3$ and A have the meanings ascribed to them in the Claims and in the text, to processes for their production as well as to the use of benzimidazole derivatives as medicines, especially as medicines having a tryptase-inhibiting action.

BACKGROUND OF THE INVENTION

Benzimidazole derivatives, as active substances that have valuable pharmaceutical properties, are known in the prior art. Thus, the international patent application WO 98/37075 refers to benzimidazole amongst other bicyclic heterocyclic compounds which, because of their thrombin-inhibiting action, can be effectively administered for the prevention and treatment of venous and arterial thrombotic illnesses.

In addition, the international patent application WO 01/14342 proposes the use of similar benzimidazole-5-yl-carboxamides having tryptase-inhibiting action, which, however, do not contain a cyclical amine of the formula:

The present invention has its object to make available new tryptase inhibitors with improved tryptase-inhibiting properties, that can be administered for the prevention and treatment of inflammatory and/or allergic illnesses.

DETAILED DESCRIPTION OF THE INVENTION

Surprisingly, it was discovered that benzimidazole derivatives of the formula (I), in which $X^1$, $R^1$, $R^2$, $R^3$ and A have the meanings ascribed to them below, have a higher tryptase-inhibiting action and can, according to the invention, be used for the prevention and treatment of illnesses in which tryptose-inhibitors can be of therapeutic value.

The present invention, therefore, relates to benzimidazole derivatives of the formula (I)

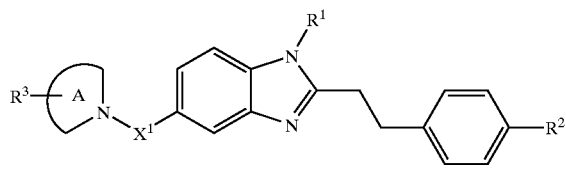

(I)

in which
$R^1$ represents a $C_1$–$C_{10}$-Alkyl- or $C_3$–$C_6$-cyclo-alkyl-group that can, whenever required, be substituted once, twice or three times by one or more of the groups comprising $C_1$–$C_4$-alkoxy, phenoxy, hydroxy-phenoxy, $C_1$–$C_4$-alkoxy-phenoxy, $C_3$–$C_6$-cyclo-alkyl, —$NH_2$, NH—($C_1$–$C_4$-alkyl), —N($C_1$–$C_4$-alkyl)$_2$, —NH—CO—($C_1$–$C_4$-Alkyl), —CO—$NH_2$, —CO—NH—($C_1$–$C_4$-alkyl) or —NH—CO-benzyl, or represents a phenyl-$C_1$–$C_4$-alkyl group in which the phenyl ring can, if necessary, be substituted once, twice or three times by one or more of the $C_1$–$C_4$-alkyl, $CF_3$, fluorine, chlorine, bromine, COOH or COO—$C_1$–$C_4$-alkyl groups, or represents a 5-, 6- or 7-membered, saturated or unsaturated heterocyclic group that is linked via a single bond or via a $C_1$–$C_4$-alkylene bridge, and that contains one, two or three heteroatoms selected from oxygen, nitrogen and sulphur, and which may be optionally substituted once, twice or three times by any one or more of the following radicals: $C_1$–$C_4$-alkyl, phenyl optionally substituted by $C_1$–$C_4$-alkyl, or benzyl optionally substituted by $C_1$–$C_4$-alkyl; or said 5-, 6- or 7-membered, saturated or unsaturated heterocyclic group is optionally condensed via two adjacent carbon atoms with a benzene ring;

$R^2$ represents —C(=NH)$NH_2$ or —$CH_2$—$NH_2$;

$X^1$ represents —CO—;

A represents a 4- or 7-membered, saturated heterocyclic group that can contain one or two nitrogen atoms and, if required, one or two hetero-atoms selected from the group comprising oxygen and sulphur;

$R^3$ represents a radical selected from the groups (a), (b) and (c):

(a) —$NR^4R^5$;
in which
$R^4$ represents hydrogen or a residue having the formula

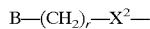

B—($CH_2$)$_r$—$X^2$— in which
B is $C_1$–$C_6$-alkyl, $C_1$–$C_6$-haloalkyl, $C_2$–$C_6$-alkenyl, $C_2$–$C_6$-alkinyl, $C_1$–$C_6$-alkoxy-$C_1$–$C_6$-alkyl, $C_3$–$C_8$-cycloalkyl, phenyl, naphthyl or a 5- or 6-membered nitrogen-, oxygen- and/or sulphur-containing heterocyclic group, whereby in each case the phenyl, naphthyl or heterocyclic group can be substituted by one or more Groups selected from halogen, nitro, cyano, $C_1$–$C_4$-alkyl, $C_1$–$C_4$-alkoxy, $C_1$–$C_4$-alkylthio, $C_1$–$C_4$-alkyl-$SO_2$—, $C_1$–$C_4$-alkyl-$PO_2$—O—, $C_1$–$C_5$-alkanoyl, $C_1$–$C_4$-alkoxycarbonyl, $C_1$–$C_4$-haloalkyl, $C_1$–$C_4$-haloalkoxy, $C_1$–$C_4$-haloalkylthio, $C_1$–$C_4$-cyanoalkyl, $C_1$–$C_4$-hydroxyalkyl, $C_1$–$C_4$-alkoxy-$C_1$–$C_4$-alkyl, carboxy, amino, $C_1$–$C_4$-alkylamino, di-($C_1$–$C_4$-alkyl)-amino, aminosulfonyl, phenyl and hydroxy groups, or represents a phenyl group in which two neighbouring carbon atoms are substituted by a $C_1$–$C_4$-alkylene-dioxy group;

$X^2$ is CO, NH—CO, $SO_2$, NH—$SO_2$ or a single bond, and r is 0 or a whole number from 1 and 4

$R^5$ represents hydrogen or a residue having the formula:

D—$(CH_2)_t$— in which

D is $C_1$–$C_6$-alkyl, $C_1$–$C_6$-haloalkyl, $C_2$–$C_6$-alkenyl, $C_2$–$C_6$-alkinyl, $C_1$–$C_6$-alkoxy-$C_1$–$C_6$-alkyl, $C_3$–$C_8$-cycloalkyl, phenyl, naphthyl or a 5- or 6-member nitrogen-, oxygen- and/or a heterocyclic group, in which each of the phenyl, naphthyl or heterocyclic groups can be replaced by one or more groups selected from halogen, nitro, cyano, $C_1$–$C_4$-alkyl, $C_1$–$C_4$-alkoxy, $C_1$–$C_4$-alkylthio, $C_1$–$C_4$-alkyl-$SO_2$—, $C_1$–$C_4$-alkyl-$PO_2$—O—, $C_1$–$C_5$-alkanoyl, $C_1$–$C_4$-alkoxycarbonyl, $C_1$–$C_4$-haloalkyl, $C_1$–$C_4$-haloalkoxy, $C_1$–$C_4$-haloalkylthio, $C_1$–$C_4$-cyanoalkyl, $C_1$–$C_4$-hydroxyalkyl, $C_1$–$C_4$-alkoxy-$C_1$–$C_4$-alkyl, carboxy, amino, $C_1$–$C_4$-alkylamino, di-($C_1$–$C_4$-alkyl)-amino, aminosulfonyl, phenyl und hydroxy, or is a phenyl group in which two neighbouring carbon atoms are substituted by a $C_1$–$C_4$-alkylene-dioxy-group, and t is 0 or a whole number from 1 to 4, or $R^4$ and $R^5$ together with the nitrogen atom form a 4- to 10-membered, saturated heterocyclic group or spiro-heterocyclic group, which can optionally contain a further hetero atom selected from oxygen, nitrogen and sulphur, in which one or two $CH_2$ groups can be replaced by C=O or C=S, and which may be substituted by any one or more of the radicals selected from: $C_1$–$C_4$-alkyl, $C_3$–$C_8$-cycloalkyl, benzyl optionally substituted by $C_1$–$C_4$-alkyl, pyridyl and phenyl optionally substituted by $C_1$–$C_4$-alkyl, $C_1$–$C_4$-alkoxy or hydroxy;

(b) —E-phenyl, in which E represents —$CH_2CH_2$— or —CH=CH—;

(c) phenyl, which is substituted by one or more substituents selected from the group comprising halogen atoms, trifluoro-methyl groups and nitro groups; if required, in the form of their tautomers, their racemates, their enantiomers, their dia-stereomeres and mixtures thereof, as well as, if required, their pharmacologically unobjectionable acid-addition salts.

The alkyl groups considered for use (including those that are components of other radicals, especially of alkoxy), may, unless otherwise defined, be branched or unbranched alkyl-groups having from 1 to 12 carbon atoms, preferably 1 to 8 carbon atoms, more preferably 1 to 6 carbon atoms, especially having 1 to 4 carbon atoms. These may, for example, be methyl, ethyl, propyl, butyl, pentyl, hexyl etc. groups. Unless otherwise indicated, the aforesaid definitions include, for example, any of their possible isomeric forms. For example, the definition propyl includes the isomeric radicals n-propyl and iso-propyl, the definition butyl includes n-butyl, iso-butyl, sec.butyl and tert.butyl, the definition pentyl includes iso-pentyl, neo-pentyl etc. If required, the definitions of the afore-mentioned alkyl groups can also be identified by their abbreviations such as Me for methyl, Et for ethyl etc.

The halo-alkyl groups considered for use (also where they are components of other radicals, especially of haloalkoxy groups) are, unless otherwise defined, branched or un-branched halo-alkyl groups having 1 to 12 carbon atoms, preferably 1 to 6 carbon atoms, more preferably having 1 to 3 carbon atoms, that are substituted by at least one halogen atom, especially the fluorine atom. These are preferably fluorinated radicals having the formula —$(CH_2)_p$—$(CF_2)_q$—Y in which p is 0 or a whole number from 1 to 4, q is a whole number from 1 to 4, and Y represents hydrogen or fluorine.

These are, for example, trifluoro-methyl, trifluoro-methoxy, difluoro-methyl, difluoro-methoxy, perfluoro-ethyl, 2,2,2-trifluoro-ethyl, 2,2,2-trifluoro-ethoxy, 1,1,1-trifluoro-prop-2-yl, etc.

The alkenyl groups used (also as components of other radicals) are branched or un-branched alkenyl groups having 2 to 12 carbon atoms, preferably 2 to 6 carbon atoms, especially 2 to 4 carbon atoms, so long as they contain at least one double bond, also, for example, the above-mentioned alkyl groups so long as they contain at least one double bond, such, for example, as vinyl (as long as no unstable enamine or enolether is formed), propenyl, iso-propenyl, butenyl, pentenyl, hexenyl.

The alkynyl; groups used (also as components of other radicals) are alkynyl groups having 2 to 12 carbon atoms, preferably 2 to 6 carbon atoms, especially 2 to 4 carbon atoms, so long as they contain at least one triple bond, such, for example, as ethinyl, propargyl, butinyl, pentinyl, hexinyl.

The halogen used is generally fluorine, chlorine, bromine or iodine.

The expression "5- or 6- or 7-membered nitrogen-, oxygen-, and/or sulphur-containing heterocyclic groups" as used in the $R^1$, B or D radicals, generally refers to an aromatic or saturated radical having 5, 6 or 7 atoms in the ring, in which at least one ring atom is a hetero-atom selected from the group N, O and S, which can, if required, be condensed with a further ring system.

The expression "4- to 10-membered heterocyclic group" as used in A and, together with the enclosed nitrogen atom, for the $R^5$ and $R^6$, generally refers to a saturated nitrogen-containing radical that has 4 to 10, preferably 5 to 7 atoms in the ring, which, if required, may also have one or more hetero-atoms selected from the group N, O and S, and which may, if required, be condensed with a further ring system.

The expression "spiro-heterocyclic group" as used for the groups that, together with the enclosed nitrogen atom, form the $R^5$ and $R^6$, generally refers to a saturated nitrogen-containing radical having 8 to 11, preferably 9 to 10 ring atoms, which, if required, can also contain one or two hetero-atoms from the group N, 0 and S, and in which one or two $CH_2$ groups can be replaced by C=O or C=S. Preferred spiro-hetero-cyclic groups are azaspiro[4,4]-nonane, azaspiro[5,4]-decane and azaspiro[5,5]-undecane, especially 2,4-dioxo-1-oxa-3-aza-spiro[4,4]-nonane.

The preferred heterocyclic groups are, for example, acridinyl, acridonyl, alkylpyridinyl, anthraquinonyl, ascorbyl, azaazulenyl, azabenzanthracenyl, azabenzanthrenyl, azachrysenyl, azacyclazinyl, azaindolyl, azanaphthacenyl, azanaphthalenyl, azaprenyl, azatriphenylenyl, azepinyl, azinoindolyl, azinopyrrolyl, benzacridinyl, benzazapinyl, benzofuryl, benzonaphthyridinyl, benzopyranonyl, benzopyranyl, benzopyronyl, benzoquinolinyl, benzoquinolizinyl, benzothiepinyl, benzothiophenyl, benzylisoquinolinyl, bipyridinyl, butyrolactonyl, caprolactamyl, carbazolyl, carbolinyl, catechinyl, chromenopyronyl, chromonopyranyl, cumarinyl, cumaronyl, decahydroquinolinyl, decahydroquinolonyl, diazaanthracenyl, diazaphenanthrenyl, dibenzazapinyl, dibenzofuranyl, dibenzothiphenyl, dichromylenyl, dihydrofuranyl, dihydroisocumarinyl, dihydroisoquinolinyl, dihydropyranyl, dihydropyridinyl, dihydropyridonyl, dihydropyronyl, dihydrothiopyranyl, diprylenyl, dioxanthylenyl, oenantholactamyl, flavanyl, flavonyl, fluoranyl, fluoresceinyl, furandionyl, furanochromanyl, furanonyl, furanoquinolinyl, furanyl, furopyranyl, furopyronyl, heteroazulenyl, hexahydropyrazinoisoquinolinyl, hydrofuranyl, hydrofuranonyl, hydroindolyl, hydropyranyl, hydropyridinyl, hydropyrrolyl, hydroquinolinyl, hydrothiochromenyl, hydrothiophenyl, indolizidinyl, indolizinyl, indolonyl, isatinyl, isatogenyl, isobenzofurandionyl, isobenzfuranyl, isochromanyl, isoflavonyl, isoindolinyl, isoindolobenzazapinyl, isoindolyl, isoquinolinyl, isoquinuclidinyl, lactamyl, lactonyl, maleimidyl, monoazabenzonaphthenyl, naphthalenyl, naphthimidazopyridindionyl, naphthindolizinedionyl, naphthodihydropyranyl, naphthofuranyl, naphthyridinyl, oxepinyl, oxindolyl, oxolenyl, perhydroazolopyridinyl, perhydroindolyl, phenanthrachinonyl, phthalideisoquinolinyl, phthalimidyl, phthalonyl, piperidinyl, piperidonyl, prolinyl, parazinyl, pyranoazinyl, pyranoazolyl, pyranopyrandionyl, pyranopyridinyl, pyranochinolinyl, pyranopyrazinyl, pyranyl, pyrazolopyridinyl, pyridinethionyl, pyridinonaphthalenyl, pyridinopyridinyl, pyridinyl, pyridocolinyl, pyridoindolyl, pyridopyridinyl, pyridopyrimidinyl, pyridopyrrolyl, pyridoquinolinyl, pyronyl, pyrrocolinyl, pyrrolidinyl, pyrrolizidinyl, pyrrolizinyl, pyrrolodioazinyl, pyrrolonyl, pyrrolopyrimidinyl, pyrroloquinolonyl, pyrrolyl, quinacridonyl, quinolinyl, quinolizidinyl, quinolizinyl, quinolonyl, quinuclidinyl, rhodaminyl, spirocumaranyl, succinimidyl, sulpholanyl, sulpholenyl, tetrahydrofuranyl, tetrahydroisoquinolinyl, tetrahydropyranyl, tetrahydropyridinyl, tetrahydrothiapyranyl, tetrahydrothiophenyl, tetrahydrothipyranonyl, tetrahydrothipyranyl, tetronyl, thiaphenyl, thiachromanyl, thiadecalinyl, thianaphthenyl, thiapyranyl, thiapyronyl, thiazolopyridinyl, thienopyridinyl, thienopyrrolyl, thienothiophenyl, thiepinyl, thiochromenyl, thiocumarinyl, thiopyranyl, triazaanthracenyl, triazinoindolyl, triazolopyridinyl, tropanyl, xanthenyl, xanthonyl, xanthydrolyl, adeninyl, alloxanyl, alloxazinyl, anthranilyl, azabenzanthrenyl, azabenzonaphthenyl, azanaphthacenyl, azaphenoxazinyl, azapurinyl, azinyl, azoloazinyl, azolyl, barbituric acid, benzazinyl, benzimidazolethionyl, benzimidazolonyl, benzisothiazolyl, benzisoxazolyl, benzocinnolinyl, benzodiazocinyl, benzodioxolanyl; benzodioxolyl, benzopyridazinyl, benzothiazepinyl, benzothiazinyl, benzothiazolyl, benzoxazinyl, benzoxazolinonyl, benzoxazolyl, cinnolinyl, depsidinyl, diazaphenanthrenyl, diazepinyl, diazinyl, dibenzoxazepinyl, dihydrobenzimidazolyl, dihydrobenzothiazinyl, dihydrooxazolyl, dihydropyridazinyl, dihydropyrimidinyl, dihydrothiazinyl, dioxanyl, dioxenyl, dioxepinyl, dioxinonyl, dioxolanyl, dioxolonyl, dioxopiperazinyl, dipyrimidopyrazinyl, dithiolanyl, dithiolenyl, dithiolyl, flavinyl, furopyrimidinyl, glycocyamidinyl, guaninyl, hexahydropyrazinoisoquinolinyl, hexahydropyridazinyl, hydantoinyl, hydroimidazolyl, hydroparazinyl, hydropyrazolyl, hydropyridazinyl, hydropyrimidinyl, imidazolinyl, imidazolyl, imidazoquinazolinyl, imidazothiazolyl, indazolebenzopyrazolyl, indoxazenyl, inosinyl, isoalloxazinyl, isothiazolyl, isoxazolidinyl, isoxazolinonyl, isoxazolinyl, isoxazolonyl, isoxazolyl, lumazinyl, methylthyminyl, methyluracilyl, morpholinyl, naphthimidazolyl, oroticyl, oxathianyl, oxathiolanyl, oxazinonyl, oxazolidinonyl, oxazolidinyl, oxazolidonyl, oxazolinonyl, oxazolinyl, oxazolonyl, oxazolopyrimidinyl, oxazolyl, perhydrocinnolinyl, perhydropyrroloazinyl, perhydropyrrolothiazinyl, perhydrothiazinonyl, perimidinyl, phenazinyl, phenothiazinyl, phenoxathiinyl, phenoxazinyl, phenoxazonyl, phthalazinyl, piperazindionyl, piperazinodionyl, polyquinoxalinyl, pteridinyl, pterinyl, purinyl, pyrazinyl, pyrazolidinyl, pyrazolidonyl, pyrazolinonyl, parazolinyl, pyrazolobenzodiazepinyl, pyrazolonyl, pyrazolopyrimidinyl, pyrazolotriazinyl, pyrazolyl, pyridazinyl, pyridazonyl, pyridopyrazinyl, pyridopyrimidinyl, pyrimidinethionyl, pyrimidinyl, pyrimidionyl, pyrimidoazepinyl, pyrimidopteridinyl, pyrrolobenzodiazepinyl, pyrrolodiazinyl, pyrrolopyrimidinyl, quinazolidinyl, quinazolinonyl, quinazolinyl, quinoxalinyl, sultamyl, sultinyl, sultonyl, tetrahydrooxazolyl, tetrahydropyrazinyl, tetrahydropyridazinyl, tetrahydroquinoxalinyl, tetrahydrothiazolyl, thiazepinyl, thiazinyl, thiazolidinonyl, thiazolidinyl, thiazolinonyl, thiazolinyl, thiazolobenzimidazolyl, thiazolyl, thienopyrimidinyl, thiazolidinonyl, thyminyl, triazolopyrimidinyl, uracilyl, xanthinyl, xylitolyl, azabenzonapththenyl, benzofuroxanyl, benzothiadiazinyl, benzotriazepinonyl, benzotriazolyl, benzoxadiazinyl, dioxadiazinyl, dithiadazolyl, dithiazolyl, furazanyl, furoxanyl, hydrotriazolyl, hydroxytrizinyl, oxadiazinyl, oxadiazolyl, oxathiazinonyl, oxatriazolyl, pentazinyl, pentazolyl, pentazinyl, polyoxadiazolyl, sydonyl, tetraoxanyl, tetrazepinyl, tetrazinyl, tetrazolyl, thiadiazinyl, thiadiazolinyl, thiadiazolyl, thiadioxazinyl, thiatriazinyl, thiatriazolyl, thiatriazolyl, triazepinyl, triazinoindolyl, triazinyl, triazolinedionyl, triazolinyl, triazolyl, trioxanyl, triphenodioxazinyl, triphenodithiazinyl, trithiadiazepinyl, trithianyl or trioxolanyl.

Especially favourable are the 5-, 6- or 7-member, saturated or unsaturated heterocyclic groups, that can contain the hetero-atoms nitrogen, oxygen or sulphur, as long as they are not otherwise described in the definition, such, for example, as pyrrole, pyrroline, pyrrolidine, pyrazole, pyrazoline, pyrazolidine, imidazole, imidazoline, imidazolidine, triazole, tetrazole, pyridine, piperidine, pyridazine, pyrimidine, pyrazine, piperazine, triazine, tetrazine, morpholine, thiomorpholine, diazepane, oxazole, isoxazole, oxazine, thiazole, isothiazole, thiadiazole, oxadiazole, pyrazolidine, in which the heterocyclic.group can be substituted as indicated in the definitions.

The favoured compounds are those of the formula 1, in which $R^1$, $R^2$, A and $X^1$ have the afore-mentioned definitions, and $R^3$ represents a radical from the group (a), in which
  $R^4$ represents a radical of the formula $$B-X^2-,$$

in which
  B stands for $C_1-C_6$-Alkyl or Phenyl, whereby the Phenyl group can be substituted by one, two or three of the groups selected from a halogen, $C_1-C_4$-Alkoxy, $C_1-C_4$-Alkyl-$SO_2-$, $C_1-C_5$-Alkanoyl, $C_1-C_4$-Alkoxycarbonyl, $C_1-C_4$-Haloalkyl, $C_1-C_4$-Haloalkoxy, $C_1-C_4$-Alkoxy- $C_1$–$C_4$-alkyl, Carboxy, Amino, $C_1$–$C_4$-Alkylamino, Di-($C_1$–$C_4$-alkyl)-amino, Aminosulfonyl, Phenyl and Hydroxy, or represents a Phenyl group, in which two neighbouring carbon atoms are replaced by a $C_1$–$C_4$-Alkylene-dioxy groups $X^2$ represents a CO, NH—CO, or a single bonding, and/or $R^5$ is hydrogen or a radical of the formula D—(CH$_2$)$_t$—, in which D represents $C_1$–$C_4$-Alkyl, $C_3$–$C_6$-Cycloalkyl, Phenyl, Naphthyl or a 5- or 6-membered nitrogen, oxygen and/or sulphur-containing heterocyclic group in which the phenyl group can be substituted by one, two or three groups selected from a halogen, $C_1$–$C_4$-Alkyl-SO$_2$—, C1–C4-Haloalkyl, $C_1$–$C_4$-Haloalkoxy, Aminosulfonyl, Phenyl and Hydroxy, and in which t is 0 where D is a $C_1$–$C_4$-Alkyl group, or t is 1 or 2 where D other than a $C_1$–$C_4$-Alkyl group.

Further favoured compounds are those of the formula I, in which $R^1$ represents $C_1$–$C_{10}$-Alkyl or $C_3$–$C_6$-Cycloalkyl, which, if required, can be substituted once, twice or three times by one or more members of the group comprising $C_1$–$C_4$-Alkoxy, Phenoxy-, $C_1$–$C_4$-Alkoxy-phenoxy, Hydroxyphenoxy, $C_3$–$C_6$-Cycloalkyl, —NH$_2$, —NH($C_1$–$C_4$-Alkyl), —N($C_1$–$C_4$-Alkyl)$_2$, —NH—CO—($C_1$–$C_4$-Alkyl), —CO—NH$_2$, —CO—NH—($C_1$–$C_4$-Alkyl) or —NH—CO-Benzyl, or represents Phenyl-$C_1$–$C_4$-alkyl, in which the phenyl ring can, if required, be substituted once, twice or three times by one or more of the radicals $C_1$–$C_4$-Alkyl, CF$_3$, Fluorine, Chlorine, Bromine, COOH or COO—$C_1$–$C_4$-Alkyl, or represents a 5- or 6-membered, saturated or unsaturated heterocyclic group that is linked via a single bond or via a $C_1$–$C_4$ alkylene bridge, and that contains one, two or three heteroatoms selected from oxygen, nitrogen and sulphur, and which may be optionally substituted once, twice or three times by any one or more of the following radicals: $C_1$–$C_4$-alkyl, phenyl optionally substituted by $C_1$–$C_4$-alkyl, or benzyl optionally substituted by $C_1$–$C_4$-alkyl; or said 5- or 6-membered, saturated or unsaturated heterocyclic group is optionally condensed via two adjacent carbon atoms with a benzene ring;

$R^2$ represents —C(=NH)NH$_2$ or —CH$_2$—NH$_2$;

A represents piperidine or piperazine;

$R^3$ represents a radical selected from the Group (a), (b) and (c);

(a) is —NR$^4$R$^1$, in which

R$^4$ represents B—X$^2$, in which

B stands for $C_1$–$C_6$-alkyl, phenyl, pyridyl, naphthyl or dihydrobenzo[1,4]dioxinyl, in which the phenyl, naphthyl, benzo or pyridyl group respectively can be substituted one or more times by halogen, cyano, $C_1$–$C_4$-alkyl, $C_1$–$C_4$-alkoxy, $C_1$–$C_4$-alkyl-SO$_2$—, $C_1$–$C_4$-alkyl-PO$_2$—O—, $C_1$–$C_4$-alkanoyl, $C_1$–$C_4$-alkoxycarbonyl, $C_1$–$C_4$-haloalkyl, $C_1$–$C_4$-haloalkoxy, phenyl, amino, $C_1$–$C_4$-alkylamino, di-($C_1$–$C_4$-alkyl)-amino, aminosulphonyl, carboxy or hydroxy;

$X^2$ represents —CO—, —NH—CO— or a single bond, $R^5$ represents hydrogen or methyl group; or $R^4$ and $R^5$ together with the nitrogen atom form a 5- or 6-member saturated hetrocyclic group or a 9- or 10-member spiro-heterocyclic group, that can contain a further hetero atom selected from the group oxygen or nitrogen, in which one or two CH$_2$ groups can be replaced by C=O, and, if required, by one or more of the radicals C1–$C_4$-alkyl, $C_5$–$C_6$-cycloalkyl, benzyl, which, if required, can be substituted by $C_1$–$C_4$-alkyl, pyridyl or phenyl, that can, if required, be substituted by $C_1$–$C_4$-alkyl, $C_1$–$C_4$-alkoxy- or hydroxy group, (a) is —E-Phenyl, in which E stands for —CH$_2$CH$_2$— or —CH=CH—;

(b) is Phenyl, which is substituted by one or two substituents selected from the group comprising fluorine, chlorine, trifluoromethyl- and nitro-; if required, in the form of their tautomers, their racemates, their enantiomers, their diastereoisomers and mixtures thereof, as well as, if required, by their pharmacologically unobjectionable acid addition salts.

Especially favoured are those compounds of the formula (I), in which $R^1$ stands for unsubstituted $C_1$–$C_{10}$-alkyl or $C_3$–$C_6$-cycloalkyl, or for a $C_1$–$C_4$-alkyl group that is substituted once or twice $C_1$–$C_4$-alkoxy, phenoxy-, $C_1$–$C_4$-alkoxy-phenoxy, hydroxyphenoxy, $C_3$–$C_6$-cycloalkyl, —NH$_2$, —NH($C_1$–$C_4$-alkyl), —N($C_1$–$C_4$-alkyl)$_2$, —NH—CO—($C_1$–$C_4$-alkyl), —CO—NH$_2$, —CO—NH—($C_1$–$C_4$-alkyl) or —NH—CO-Benzyl, or for Phenyl-$C_1$–$C_3$-alkyl, in which the phenyl ring may, if required, be substituted once or twice by $C_1$–$C_4$-alkyl, CF$_3$, Fluorine, Chlorine, Bromine, COOH or COO—$C_1$–$C_4$-alkyl, or for represents a 5-, 6- or 7-membered, saturated or unsaturated heterocyclic group that is linked via a $C_1$–$C_3$-alkylene bridge, and contains one or two heteroatoms selected from oxygen, nitrogen and sulphur, and which is optionally substituted once or twice by any one or more of the radicals methyl, ethyl, propyl, phenyl, methylphenyl or benzyl, or said heterocyclic group is optionally condensed via two adjacent carbon atoms with a benzene ring;

$R^2$ represents —C(=NH)NH$_2$ or —CH$_2$—NH$_2$;

A represents piperidine-1,4-diyl or Piperazine-1,4-diyl;

$R^3$ represents a radical selected from the groups (a), (b) and (c):

(a) —NR$^4$R$^5$, in which

R$^4$ represents $C_1$–$C_6$-alkylaminocarbonyl, phenylcarbonyl, pyridylcarbonyl, phenylaminocarbonyl or dihydrobenzo[1,4]dioxinylcarbonyl, in which each phenyl, benzo or pyridyl group can be substituted once or twice by the halogen, $C_1$–$C_4$-alkyl, $C_1$–$C_4$-alkoxy, $C_1$–$C_4$-alkylthio, $C_1$–$C_5$-alkanoyl, $C_1$–$C_4$-alkoxycarbonyl, $C_1$–$C_4$-haloalkyl, $C_1$–$C_4$-haloalkoxy, $C_1$–$C_4$-haloalkylthio, carboxy or hydroxy group;

R$^5$ stands for hydrogen or Methyl; or

R$^4$ and R$^5$ together with the nitrogen atom form a 5-membered saturated heterocyclic group or a 9-membered spiroheterocyclic group, which can contain an additional hetero atom selected from oxygen and nitrogen, in which one or two CH$_2$ groups are replaced by C=O, and which is optionally substituted by any one or more of the radicals selected from: $C_1$–$C_4$-alkyl, $C_5$–$C_6$-cycloalkyl, benzyl optionally substituted by $C_1$–$C_4$-alkyl, pyridyl and phenyl optionally substituted by $C_1$–$C_4$-alkyl, $C_1$–$C_4$-alkoxy or hydroxy;

(b) —E-Phenyl, in which
E stands for —$CH_2CH_2$— or —CH=CH—;

(c) Phenyl, which is substituted by one or two substituents selected from the group comprising fluorine, chlorine, trifluoromethyl and nitro;

or, if required, in the form of their tautomere, racemate, enantiomere, diastereomere or mixtures thereof, or, if required, as their pharmacologically unobjectionable acid-addition salts, In Addition, Preferred Compounds Also Include Those of Formula (I), in Which $R^2$, $R^3$, $X^1$ and A Have the Afore-mentioned Meanings, and $R^1$ represents unsubstituted $C_1$–$C_{10}$-alkyl or $C_3$–$C_6$-cycloalkyl, or by $C_1$–$C_4$-alkoxy-phenoxy, hydroxy-phenoxy, $C_3$–$C_6$-cyclo-alkyl, —$NH_2$, —NH($C_1$–$C_4$-alkyl), —N($C_1$–$C_4$-alkyl)$_2$, —NH—CO—($C_1$–$C_4$-alkyl), —CO—$NH_2$, —CO—NH—($C_1$–$C_4$-alkyl) or $C_1$–$C_4$-alkyl-substituted by —NH—CO-benzyl, or phenyl-$C_1$–$C_3$-alkyl, whereby the phenyl ring can, if required, be substituted once or twice by $C_1$–$C_4$-alkyl, $CF_3$, fluorine, chlorine, bromine, COOH or COO—$C_1$–$C_4$-alkyl groups, or represents a heterocyclic compound that is linked via a $C_1$–$C_3$-alkylene bridge, that can, if required, by substituted once or twice by one or more of the radicals methyl, ethyl, propyl, phenyl, methyl-phenyl- or benzyl, and that is selected from the group pyrrole, pyrroline, pyrrolide, pyridine, piperidine, pyrimidine, piperizine, morpholine, thio-morpholine, imidazole, imidazoline, imidazolidine, pyrazole, pyrazoline, pyrazolidine, triazole, furane, tetra-hydro-furane, α-pyrane, γ-pyrane, dioxolane, tetra-hydro-pyrane, dioxane, thiophene, dihydro-thiophene, thiolane, dithiolane, oxazole, isoxazole, thiazole, isothiazole, oxadiazole, benzodioxol, benzimidazole, benzthiophene, benzfuran and indole.

Especially favoured are the compounds having the formula (I), in which $R^2$, $R^3$, $X^1$ and A have the afore-mentioned designations, and $R^1$ stands for methyl, ethyl, propyl, butyl, pentyl, hexyl, heptyl, octyl, nonyl, decyl, cyclopropyl, cyclopentyl or cyclohexyl, or for a methyl-, ethyl- or propyl-group that is substituted by methoxy, ethoxy, cyclopropyl, cyclopentyl, cyclohexyl, phenyl, methoxy-phenoxy, or stands for benzyl that is substituted once or twice by methyl, ethyl, propyl, $CF_3$, fluorine, chlorine, bromine, COOH, COOMe or COOEt, stands for phenylethyl that is substituted once or twice by methyl, ethyl, propyl, $CF_3$, fluorine, chlorine, bromine, COOH, COOMe or COOEt, or for a heterocyclic group that is connected via a methylene-, ethylene- or propylene-bridge, and that is, if required, substituted once or twice by one or more of the radicals methyl, ethyl, propyl, phenyl, methyl-phenyl or benzyl, and that is selected from the group pyrrole, pyrrolidine, pyridine, piperidine, piperazine, morpholine, furane, tetrahydro-furane, thiophene, benzodioxole and benzimidazole.

An especially favoured form of the compound are the compounds of the formula (I), in which $R^2$, $E^3$, $X^1$ and A have the afore-mentioned meanings, and $R^1$ represents methyl, ethyl, propyl, pentyl, n-decyl, cyclopropyl or cyclohexyl, or for a methyl-, ethyl or propyl-radical that is substituted by methoxy, ethoxy, cyclopropyl, cyclopentyl, cyclohexyl, phenyl or methoxy-phenoxy, or for benzyl that is substituted by methyl, $CF_3$, COOH, COOMe or COOEt, or for tetrahydrofurane that is connected via a methylene bridge.

Further favoured compounds are those having the formula (I) in which $R^2$, $R^3$, $X^1$ and A have the afore-mentioned meanings, and $R^1$ represents methyl, ethyl, propyl, pentyl, cyclopropyl, phenyl-ethyl, phenyl-propyl, cyclopropyl-methyl, tetrahydro-furanyl-methy or benzyl, that is substituted once or twice by $CF_3$, COOH, COOMe or COOEt.

Most favoured compounds are those of formula (I) in which $R^2$, $R^3$, $X^1$ and A have the afore-mentioned meanings especially where $R^1$ is methyl or cyloprogyl, and $R^2$ is —C(=NH)$NH_2$.

Most especially favoured are the compounds of the formula (IA)

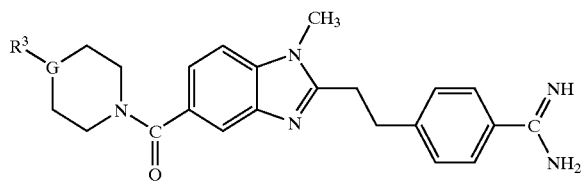

(1A)

in which $R^3$ has the afore-mentioned meaning, and

G is CH or N.

Especially good results have been obtained with the compounds of formula I or IA that are selected from the group comprising

[2-(4-Amidinophenyl)-ethyl]-1-methyl-benzimidazole-5-yl-carboxylic acid-[4-(3-phenyl-allyl)-piperazinyl]-amide-dihydrochloride

[2-(4-Amidinophenyl)-ethyl]-1-methyl-benzimidazole-5-yl-carboxylic acid-[4-(2-nitro-4-trifluoromethyl-phenyl)-piperazinyl]-amid-dihydrochloride

[2-(4-Amidinophenyl)-ethyl]-1-methyl-benzimidazole-5-yl-carboxylic acid-[(2-cyclohexyl-ethyl)-piperazinyl]-amid-dihydrochloride

[2-(4-Amidinophenyl)-ethyl]-1-methyl-benzimidazole-5-yl-carboxylic acid-[4-(5-benzyl-2,4-dioxo-oxazolidine-3-yl)-piperidinyl]-amide-hydrochloride

[2-(4-Amidinophenyl)-ethyl]-1-methyl-benzimidazole-5-yl-carboxylic acid-{4-[2-benzoylamino-(2,3-dihydro-benzo[1,4]dioxine)]-piperydinyl}-amide-hydrochloride

[2-(4-Amidinophenyl)-ethyl]-1-methyl-benzimidazole-5-yl-carboxylic acid-[4-(2-oxo-3-phenyl-imidazolidine-1-yl)-piperidinyl]-amide-hydrochloride

[2-(4-Amidinophenyl)-ethyl]-1-methyl-benzimidazole-5-yl-carboxylic acid-[4-(2,4-dioxo-1-oxa-3-aza-spiro[4,4]non-3-yl)-piperidinyl]-amide-hydrochloride

[2-(4-Amidinophenyl)-ethyl]-1-methyl-benzimidazole-5-yl-carboxylic acid-[4-(4-fluorobenzamido)-piperazinyl]-amid-hydrochloride

[2-(4-Amidinophenyl)-ethyl]-1-methyl-benzimidazole-5-yl-carboxylic acid-[4-(4-nitrophenyl)-piperazinyl]-amide-dihydrochloride

[2-(4-Amidinophenyl)-ethyl]-1-methyl-benzimidazole-5-yl-carboxylic acid-[4-(2-pyridylamido)-piperidinyl]-amide-dihydrochloride

[2-(4-Amidinophenyl)-ethyl]-1-methyl-benzimidazole-5-yl-carboxylic acid-[4-(3-butyl-ureido)-piperidinyl]-amide-hydrochloride

[2-(4-Amidinophenyl)-ethyl]-1-methyl-benzimidazole-5-yl-carboxylic acid-[4-(2,4-dioxo-5-propyl-oxazolidine-3-yl)-piperidinyl]-amide-hydrochloride

[2-(4-Amidinophenyl)-ethyl]-1-methyl-benzimidazole-5-yl-carboxylic acid-(4-benzamido-piperidinyl)-amide-hydrochloride

[2-(4-Amidinophenyl)-ethyl]-1-methyl-benzimidazole-5-yl-carboxylic-{4-[3-(2,3-dichloro-phenyl)-ureido]-piperidinyl}-amide-hydrochloride 2-[2-(4-Aminomethylphenyl)-ethyl]-1-methyl-benzimidazole-5-yl-carboxylic acid-(4-benzamidopiperidinyl)-amide 2-[2-(4-Amidinophenyl)-ethyl]-1-(3-ethoxy-propyl)-benzimidazole-5-yl-carboxylic acid-(4-phenethyl-piperazinyl)-amide-dihydrochloride 2-[2-(4-Amidinophenyl)-ethyl]-1-(3-ethoxy-propyl)-benzimidazole-5-yl-carboxylic acid-(4-benzamidopiperidinyl)-amide-hydrochloride 2-[2-(4-Amidinophenyl)-ethyl]-1-(3-ethoxy-propyl)-benzimidazole-5-yl-carboxylic acid-[4-(3-phenyl-allyl)-piperazinyl]-amide-hydrochloride 2-[2-(4-Amidinophenyl)-ethyl]-1-(3-ethoxy-propyl)-benzimidazole-5-yl-carboxylic acid-[4-(3-phenyl-allyl)-piperazinyl]-amide-trihydrochloride 2-[2-(4-Amidinophenyl)-ethyl]-1-(3-ethoxy-propyl)-benzimidazole-5-yl-carboxylic acid-[4-(3-phenyl-ureido)-piperidinyl]-amide-dihydrochloride 2-[2-(4-Amidinophenyl)-ethyl]-1-(3-ethoxy-propyl)-benzimidazole-5-yl-carboxylic acid-{4-[2-benzoylamino-(2,3-dihydro-benzo[1,4]dioxin)]-piperydinyl}-amide-dihydrochloride 2-[2-(4-Amidinophenyl)-ethyl]-1-(3-ethoxy-propyl)-benzimidazole-5-yl-carboxylic acid-[4-(5-benzyl-2,4-dioxo-oxazolidine-3-yl)-piperidinyl]-amide-dihydrochloride 2-[2-(4-Amidinophenyl)-ethyl]-1-(3-ethoxy-propyl)-benzimidazole-5-yl-carboxylic acid-[(2-cyclohexyl-ethyl)-piperazinyl]-amide-trihydrochloride 2-[2-(4-Amidinophenyl)-ethyl]-1-methyl-benzimidazole-5-yl-carboxylic acid-[4-(3-chloro)-benzamidopiperidinyl)-amide 2-[2-(4-Amidinophenyl)-ethyl]-1-methyl-benzimidazole-5-yl-carboxylic acid-[4-(3-brom)-benzamidopiperidinyl)-amide 2-[2-(4-Amidinophenyl)-ethyl]-1-methyl-benzimidazole-5-yl-carboxylic acid-[4-(2-hydroxy)-benzamidopiperidinyl)-amide 2-[2-(4-Amidinophenyl)-ethyl]-1-methyl-benzimidazole-5-yl-carboxylic acid-[4-(2-difluoromethylsulfanyl)-benzamidopiperidinyl)-amide 2-[2-(4-Amidinophenyl)-ethyl]-1-methyl-benzimidazole-5-yl-carboxylic acid-[4-(3-difluoromethylsulfanyl)-benzamidopiperidinyl)-amide 2-[2-(4-Amidinophenyl)-ethyl]-1-methyl-benzimidazole-5-yl-carboxylic acid-[4-(2,3-dichloro)-benzamidopiperidinyl)-amide 2-[2-(4-Amidinophenyl)-ethyl]-1-methyl-benzimidazole-5-yl-carboxylic acid-[4-(2-methoxy)-benzamidopiperidinyl)-amide 2-[2-(4-Amidinophenyl)-ethyl]-1-methyl-benzimidazole-5-yl-carboxylic acid-[4-(2-bromo)-benzamidopiperidinyl)-amide 2-[2-(4-Amidinophenyl)-ethyl]-1-methyl-benzimidazole-5-yl-carboxylic acid-[4-(2-chloro)-benzamidopiperidinyl)-amide 2-[2-(4-Amidinophenyl)-ethyl]-1-methyl-benzimidazole-5-yl-carboxylic acid-[4-(N-methyl)benzamidopiperidinyl]-amide 2-[2-(4-Amidinophenyl)-ethyl]-1-methyl-benzimidazole-5-yl-carboxylic acid-(4-anilinopiperidinyl)-amide 2-[2-(4-Amidinophenyl)-ethyl]-1-methyl-benzimidazole-5-yl-carboxylic acid-{4-[3-(2,3-dichloro)-phenyl-1-methyl-ureido]piperidinyl}-amide 2-[2-(4-Amidinophenyl)-ethyl]-1-methyl-benzimidazole-5-yl-carboxylic acid-{4-[3-(3-acetyl)-phenylureido]piperidinyl}-amide 2-[2-(4-Amidinophenyl)-ethyl]-1-methyl-benzimidazole-5-yl-carboxylic acid-{4-[3-(3-carboxyl)-phenylureido]piperidinyl}-amide 2-[2-(4-Amidinophenyl)-ethyl]-1-methyl-benzimidazole-5-yl-carboxylic acid-{4-[3-(3-methoxycarbonyl)phenylureido]piperidinyl}-amide 2-[2-(4-Methoxycarbonylamidinophenyl)-ethyl]-1-methyl-benzimidazole-5-yl-carboxylic acid-{4-[3-(3-methoxycarbonyl)phenylureido]piperidinyl}-amide 2-[2-(4-Isobutoxycarbonylamidinophenyl)-ethyl]-1-methyl-benzimidazole-5-yl-carboxylic acid-{4-[3-(3-methoxycarbonyl)phenylureido]piperidinyl}-amide 2-[2-(4-Amidinophenyl)-ethyl]-1-methyl-benzimidazole-5-yl-carboxylic acid-{4-[3-(3-methylsulfanyl)phenylureido9piperidinyl}-amide 2-[2-(4-Amidinophenyl)-ethyl]-1-methyl-benzimidazole-5-yl-carboxylic acid-{4-[3-(3-iodo)-phenylureido]piperidinyl}-amide 2-[2-(4-Amidinophenyl)-ethyl]-1-methyl-benzimidazole-5-yl-carboxylic acid-{4-[3-(3-chloro)-phenylureido]piperidinyl}-amide 2-[2-(4-Amidinophenyl)-ethyl]-1-methyl-benzimidazole-5-yl-carboxylic acid-{4-[3-(3-methoxycarbonyl)-phenyl-1-methyl-ureido]piperidinyl)-amide if required, in the form of their tautomers, racemates, enantiomers, diastereoisomers and mixtures thereof, as well as, if required, their pharmacologically unobjectionable acid addition salts.

In addition to the afore-mentioned compounds of the general formula (I), the present invention also has the object of the production of compounds that, in view of the transformation in vivo of the compounds into their cleavable functionality of the therapeutically effective compounds of the general formula (I) by the organs only after ingestion by the patient. Such compounds are referred to as 'Pro-drugs'. A further object of the invention is, therefore, the poroduction of pro-drugs of the formula (II)

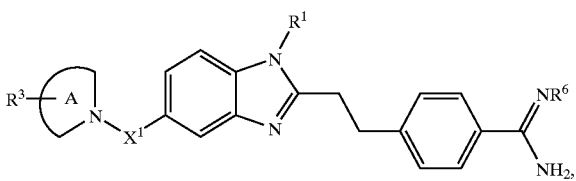

(II)

in which

R$^1$, R$^3$, A and X$^1$ have the meanings ascribed to them in the Claims 1 to 11; and R$^6$ stands for a radical that is split off under physiological conditions in man or animal bodies, preferably under the influence of proteases, to release the corresponding compound of the formula I., if required, in the form of their tautomers, racemates, enantiomers or diastereoisomers or mixtures thereof, or, if required, as their pharmacologically unobjectionable acid-addition salts.

Preferably, $R^6$ represents Hydroxy, $C_1$-$C_8$-Alkoxy, —O—CO—$C_1$-$C_8$-Alkyl, O—CO—O—$C_1$-$C_8$-Alkyl, —CO—(O)$_s$—$C_1$-$C_8$-Alkyl, —CO—(O)$_s$—$C_1$-$C_4$-Haloalkyl, —CO—(O)$_s$—$C_1$-$C_4$-Alkyl-O—CO—$C_1$-$C_4$-Alkyl, —CO—(O)$_s$-Phenyl, —CO—(O)$_s$-Pyridyl, —CO—(O)$_s$—$C_2$-$C_4$-Alkenyl-Phenyl or —CO—(O)$_s$—$C_1$-$C_4$-Alkyl-Phenyl, whereby, the phenyl ring in each of the above-named groups can be substituted by halogen, $C_1$-$C_4$-alkyl, $C_1$-$C_4$-haloalkyl, $C_1$-$C_4$-alkylamine, di-($C_1$-$C_4$-alkyl)-amine, $C_1$-$C_4$-alkoxy, $C_1$-$C_4$-alkanoyl, $C_1$-$C_4$-alkanoyloxy or $C_1$-$C_4$-haloalkoxy, and s is 0 or 1, especially where $R^6$ represents hydroxy, methoxycarbonyl, ethoxycarbonyl, propyloxycarbonyl, butyloxycarbonyl, pentyloxycarbonyl, hexyloxycarbonyl, octyloxycarbonyl, 222-trichloerethoxycarbonyl, benzyloxycarbonyl, phenoxycarbonyl, methoxyphenoxycarbonyl, methylphenoxycarbonyl, acetyloxystibenylcarbonyl, especially 2-(ortho-acetyloxyphenyl)-ethene-1-ylcarbonyl or Phenylcarbonyl, if required, in the form of their tautomers, racemates, enantiomers or diastereoisomers or mixtures thereof, or, if required, as their pharmacologically unobjectionable acid-addition salts.

In addition, the object of the present invention is to provide a use of the above-defined compounds of the general formula (I), as well as of the pro-drugs of the general formula (II), for the production of medicines for the treatment of diseases, by which tryptase-inhibitors can promote a therapeutic value.

According to the invention, the use of the aforementioned compounds of the general formula (I) is preferred for the production of medicines for the prevention and/or treatment of inflamed and/or allergic illnesses. Especially preferred is the use of the compounds indicated at the beginning, of the general formula (I) for the production of medicines for the prevention and/or treatment of bronchial asthma, allergic rhinitis, allergic conjunctivitis, atopical dermatitis, urticaria, allergic otitis, allergic stomach-intestinal illnesses, Morbus Crohn, colitis ulcerosa, anaphylactic shock, septic shock, shock-lung (ARDS) and arthritis. It is, further, of interest, to use the compounds mentioned at the beginning, that correspond to the general formula (I) for the production of medicines for the prevention and/or treatment of illnesses having re-constructive antecedents in the respiratory passages and in the lung parenchyma, such as chronic (obstructive) bronchitis and interstitial lung diseases such as idiopathic lung fibrosis, fibrous alveolitis, sarcoidosis and histio-cytosis X, as well as other fibrous diseases such as scar tissue formation, as well as collagenoses such as lupus eryhmetodis and sclerodermy, as well as arteriosclerosis, psoriasis and neoplases.

The synthesis of aminocarbonyl-substituted benzimidazole derivatives of the formula (I), as well as those of the pro-drugs of the general formula (II) is facilitated by reference to the synthesis known from the prior art. In this connection, reference can be made to the international patent applications WO 98/37075 and WO 01/14342 referred to at the beginning, the contents of which are specifically noted at this point.

A further aspect of the invention has as objective the compounds of the general formula (III)

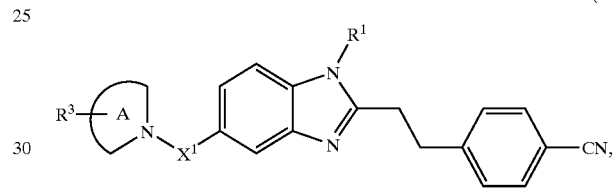

(III)

in which the radicals $X^1$, $R^1$, $R^3$ and A can have the meanings as indicated above. The compounds of the general formula (III) represent valuable intermediary products for the production according to the invention of aminocarbonyl-substituted benzimidazole derivatives of the general formula (I), as well as of prodrugs of the invention having the general formula (II).

A possible access to the compounds of the invention having the formula I through the use of conventional chemical synthetic methods is schematically presented in Scheme I:

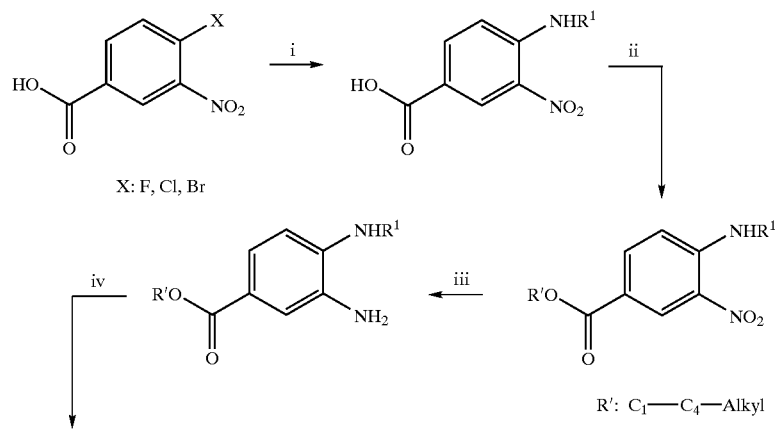

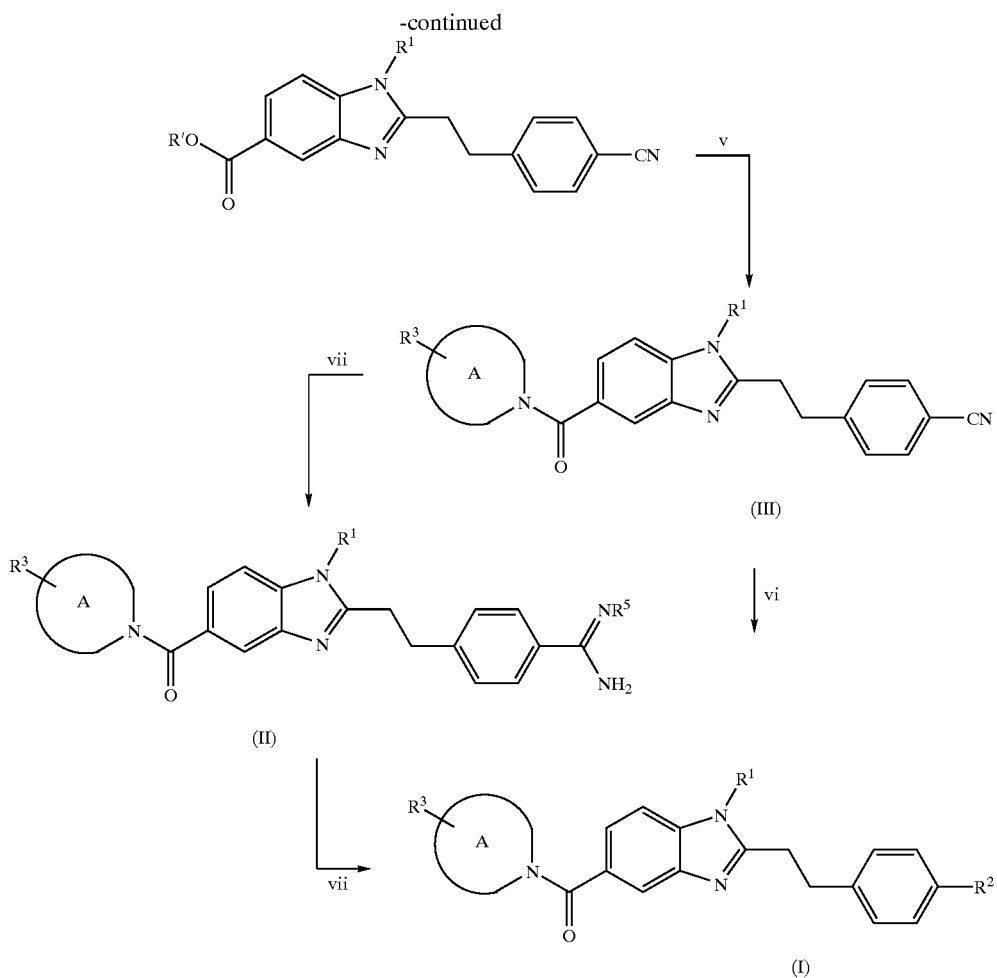

In a first synthesising stage (Stage i), starting from 4-halogen-3-nitro-benzoic acid derivatives, through aminolysis with appropriate substituted amines, the synthesis of 4-amino-3-nitrobenzoic acid derivatives can be achieved. The reaction is carried out in a suitable organic solvent such, for example, as dimethylsulphoxide, N,N-dimethylformamide, N-methylpyrrolidone or also, if desired, in Water at room temperature or at a temperature in the range of 30–80° C., preferably at 40–50° C. The aminobenzoic acid compounds obtained are transferred into a corresponding alkyl ester, preferably into the corresponding methyl ester or ethyl ester by conventional, standard methods, (Stage ii). The reduction of the nitro group to the diaminobenzoic acid-alkyl ester is achieved, preferably, by means of a catalytic hydrogenation in accordance with Stage iii. The catalyst used can, preferably, be palladium. Especially preferred is the use as catalyst of palladium on charcoal (5%). By reacting the diaminobenzoic ester so obtained with p-cyanophenyl-propionic acid in the presence of dehydrating reagents, the benzimidazole-heterocyclic compound is obtained in accordance with stage v (Scheme 1). The conversion is preferably carried out in a solvent or mixture of solvents such, for example, as methylenchloride, dimethylformamide, Benzene, Toluene, Chlorobenzene, tetrahydrofurane, benzene/tetrahydrofurane or dioxan. As dehydrating agent can be considered chloro-formic acid-isobutyl ester, ortho-carbonic acid-tetraethylester, ortho-acetic acid-trimethylester, 2,2-dimethoxypropane, tetramethoxysilane, phosphorus oxychloride, thionyl chloride, trimethyl chlorsilane, phosphorus trichloride, phosphorus pentoxide, 1,2-Dihydro-2-ethoxy-quinoline-1-carboxylic acid-ethylester (EEDQ), 1,2-dihydro-2-i-propyloxy-quinoline-1-carboxylic acid-i-propylester (IIDQ), N,N'-dicyclohexyl-carbodiimide, N,N'-dicyclohexylcarbodiimide/N-hydroxysuccinimide, N,N'-dicyclohexylcarbodiimide/1-hydroxy-benztriazole, 2-(1H-benzotriazole-1-yl)-1,1,3,3-tetramethyluronium-tetrafluoro-borat, 2-(1H-benzotriazol-1-yl)-1,1,3,3-tetramethyluronium-tetrafluoro-borate/1-hydroxy-benztriazole, N,N'-carbonyldiimidazole or Triphenylphosphine/Tetrachloro-carboxylic-carbon. If required, it may be useful to add a base such as pyridine, 4-dimethyl-amino-pyridine, N-methyl-morpholine or triethylamine. The conversion normally takes place at temperatures between 0 and 150° C., preferable at temperatures between 0 and 110° C.

The benzimidazole derivatives of the general formula (III) obtained in accordance with Stage v are either directly obtainable from the above-named benzimidazole-carboxylic acid esters or by way of the corresponding carboxylic acids or carboxylic acid halides.

In the event that the carboxylic acid esters obtained according to the Stage iv are saponified under standard conditions (protic organic solvent such, for example, as methanol, ethanol or isopropanol, if required in the presence of water, in the presence of bases such as hydroxides or carbonates of alkaline-or alkaline earth metals), this leads to the corresponding free carboxylic acids. Normally, the saponification is carried out at temperatures between 0–40° C., preferably at 10–30° C. If required, the synthesis can also be carried out at a raised temperature (reflux temperature>50° C.).

According to the invention, the preferred solvent is a methanol-water mixture. As the base used, sodium hydroxide is preferred. The conversion of the acids so obtained with the amines H—NR$^3$R$^4$ into the compounds of the general formula (III) is, if desired, carried out in a solvent or solvent mixture such as methylene chloride, dimethylformamide, Benzene, Toluene, Chlorobenzene, Tetrahydrofurane, Benzene/Tetrahydrofurane or dioxane, or in the corresponding cyclical amine of the formula

if necessary, in the presence of an dehydrating agent such, for example, as in the presence of chloroformic acid isobutylester, ortho-carboxylic acid-tetra-ethylester, ortho-acetic acid-trimethylester, 2,2-dimethoxypropane, tetramethoxysilane, thionyl chloride, trimethylchloro-silane, phosphor-trichloride, phosphor-pentoxide, N,N'-dicyclohexyl-carbodiimide, N,N'-dicyclohexyl-carbodiimide/N-hydroxy-succinimide, N,N'-Dicyclohexyl-carbodiimide/1-hydroxy-benztriazole, 2-(1H-benzotriazole-1-yl)-1,1,3,3-tetramethyl-uronium-tetrafluoroborate, 2-(1H-benzotriazole-1-yl)-1,1,3,3-tetramethyl-uronium-tetrafluoroborate/1-hydroxy-benztriazole, N,N'-Carbonyl-diimidazole or triphenylphosphine/Tetrachloro-carbon, and, if required, with the addition of a base such as pyridine, 4-dimethylamino-pyridine, N-methyl-morpholine3 or triethylamine, usefully at temperatures between 0 and 150° C., preferably at temperatures between 0 and 100° C.

The synthesis of the compounds of the general formula (III) starting from the carboxylic acid esters or from the corresponding carboxylic acid chlorides obtained in accordance with the Scheme 1 (Stage iv) is either carried out in the corresponding cyclical amine of the formula

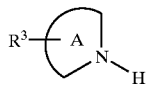

as solvent, or with this amine in the presence of a solvent such as methylene chloride, ether or ethyl acetate and, preferably, in the presence of a tertiary organic base such as triethylamine, N-ethyl-diisopropylamine or N-methyl-morpholine at temperatures between 0 and 150° C., preferably at temperatures between 40 and 100° C.

A compound of the general formula (I) is, for example, obtainable by treatment of a compound of the general formula (III, Stage vi) with a corresponding alcohol such as methanol, ethanol, n-propanol, isopropanol or benzylalcohol, if desired in a mixture with another organic solvent such, for example, as Chloroform, nitrobenzene or Toluene in the presence of an acid such as hydrochloric acid, or by reaction of a corresponding amide with a trialkyloxonium salt such as triethyloxonium-tetrafluoroborate in a solvent such as methylene chloride, tetrahydrofurane or dioxane at temperatures between −10 and 50° C., preferably, however, between 0 to 20° C. Alternatively, the compounds of the general formula (I) can be obtained by reacting a compound of the general formula (III, Stage vi) with sulphur-nucleophiles such, for example, as hydrogen sulphide, ammonium- or sodium sulphide, sodium-hydrogen sulphide, carbon disulphide, thioacetamide or bis-trimethyl-silyl-thioether, if required in the presence of bases such as triethylamine, ammonia, sodium-hydride or sodium-alcoholate in solvents such as methanol, ethanol, water, tetrahydro-furane, pyridine, dimethyl-formamide or 1,3-dimethyl-imidazolidine-2-one, at 20–100° C., and treatment with a suitable methylating agent such, for example, as methyl iodide or dimethyl sulphate, in a solvent such as Acetonitrile or Acetone, at temperatures between −10 and 50° C., but preferably at 0–20° C., and then treatment with ammonia, ammonium carbonate or ammonium chloride in a suitable alcohol such, for example, as methanol, ethanol, isopropanol etc. at temperatures between −10 and 50° C., but preferably at 0–20° C.

In addition, the compounds of the invention having the general formula (I) are obtainable by treatment of a compound of the general formula (III) with lithium-hexamethyl-disilazide in a suitable organic solvent such, for example, as tetrahydro-furane at temperatures between −20 and 50° C., but preferably at 0–20° C., and then by hydrolysis with diluted hydrochloric acid at 0–5° C.

A further alternative method of obtaining the compounds of the general formula (I) can succeed through the treatment of a compound of the general formula (III) with ammonium chloride and trimethyl-aluminium in a suitable organic solvent such, for example, as toluene, at temperatures between 20 and 150° C., but preferable at 110° C.

A compound of the general formula (II) is obtainable, for example, by treatment of a compound of the general formula III, Stage vii) with hydroxylamine in the presence of carbonates or alcoholates of alkali- or alkali-earth metals, in solvents such as methanol, ethanol, n-propanol or iso-propanol, if desired, in mixtures with dioxane or tetrahydro-furane. The alcoholates can be obtained from the respective alkali metals or metal hydrides and the corresponding alcohol. The reaction is, preferably, carried out at 20–100° C., especially preferably at the boiling point temperature of the solvent used. Compounds of the general formula (II) can, alternatively, be obtained by treatment of a compound of the general formula (III, Stage vii) with a corresponding alcohol such as methanol, ethanol, n-propanol, iso-propanol or ben-zyl alcohol, in the presence of an acid such as hydrochloric acid, or by reaction of a corresponding amide with a trialkyl-oxonium salt such as triethyl-oxonium-tetra-fluoroborate in a solvent such as methylene chloride, tetrahydro-furane or dioxane, at temperatures between −10 and 50° C., but preferably at 0–20° C., and then treatment with hydroxylamine in the presence of bases in a suitable alcohol such as methanol, ethanol, isopropanol, etc., at temperatures between −10 and 50° C., but preferably at 0–20° C.

A compound of the general formula (I) is obtained, for example, by treatment of a compound of the general formula (II, Stage viii) with hydrogen in the presence of hydrogenating catalysts such as Raney Nickel or rhodium/aluminium oxide in water or methanol, if required, with the addition of acids such as hydrochloric acid or methane-sulphonic acid, or by treatment with hydrogen in the presence of palladium/carbon in acetic acid/acetic anhydride at 20–50° C. and at 1–5 bar water pressure, preferably at room temperature and standard pressure.

Acyl- or alkoxycarbonyl-prodrugs of the compound having the general formula (I) are obtained by reaction of compounds of the general formula (I) with the corresponding acid chlorides in the presence of bases such, for example, as triethylamine, N-methyl-morpholine, diethyl-isopropylamine or DBU in a suitable solvent such as methylene chloride, chloroform, tetrahydro-furane, aceto-nitrile, dimethyl-formamide or dimethyl-sulphoxide.

The following examples describe in detail methods for the production of the compounds according to the invention. The following examples of the syntheses serve exclusively as detailed illustrations, without the subject of the invention being restricted thereto.

EXAMPLE 1

[2-(4-amidinophenyl)-ethyl]-1-methyl-benzimidazole-5-yl-carboxylic acid-[4-(3-phenyl-allyl)-piperazinyl]-amide-dihydrochloride

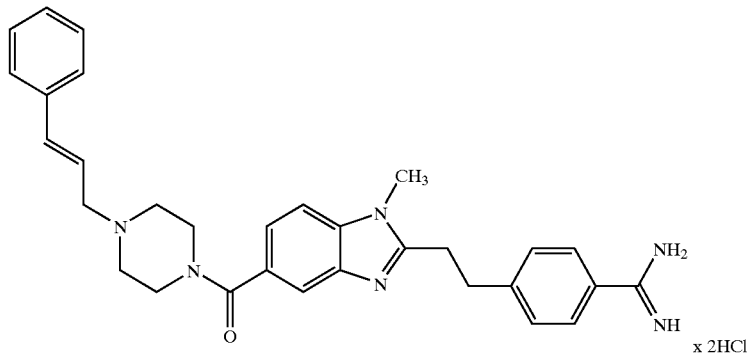

a) 4-Methylamino-3-nitrobenzoic acid:

20 g (100 mmol) of 4-Chloro-3-nitro-benzoic acid is dissolved in 80 ml of a 40% aqueous solution of methylamine, stirred for 15 hours at room temperature and for 1.5 hours at 40–50° C. After cooling, it is acidified with acetic acid. The crystals formed are filtered off, washed with cold water and dried. The yield: 18.2 g (93%); Melting point: 220° C.

b) Methylamino-3-nitro-benzoic acid-methyl ester 9.8 g (50 mmol) of 4-methylamino-3-nitro-benzoic acid are treated in 50 ml of dimethyl formamide (DMF) with $K_2CO_3$ (14 g). 5 ml of dimethyl sulphate are added dropwise to this mixture over 10 minutes with stirring. It is stirred for 15 minutes and heated for 0.5 hours at 60° C. After cooling, it is diluted with water, the precipitated solids are filtered off, washed with water and dried. Yield: 9.8 g (93%); M.Pt.: 138–140° C.

c) 3-amino-4-methylamino-benzoic acid methyl ester 71 g of 4-methylamino-3-nitro-benzoic acid-methyl ester (338 mmol) are hydrogenated in 1.41, of methanol and 67 ml of concentrated aqueous hydrochloric acid in the presence of 15 g of Pd/C (5%) at 2–5 bar, at room temperature. After filtering off the catalysts and distilling off the solvent under vacuum, the residue is dissolved in 200 ml of water, covered with ethyl acetate and basified with a 50% solution of potassium carbonate. The product is extracted in the organic phase, which is again washed with water and then dried over sodium sulphate. After removal of most of the solvent by distillation under vacuum, diethyl ether is added and it is cooled off. The resulting crystals are filtered off. Yield: 54 g (81%); MPt.: 215–220° C. (decomposition).

d) 2-[2-(4-Cyanophenyl)-ethyl]-1-methyl-benzimidazole-5-yl-carboxylic acid methyl ester:

7.5 g of 3-Amino-4-methylamino-benzoic acid-methylester (42 mmol) and 7.3 g p-cyano-phenyl-propionic acid (42 mmol) are dissolved in 50 ml of phosphorus oxychloride and heated under reflux for 2 hours. After cooling, the excess phosphorus oxychloride is treated with ice-water. It is covered with ethyl acetate and basified with potassium carbonate, with stirring. The organic phase is separated, washed with water and dried. After distilling off most of the solvent under vacuum, it is cooled off. The precipitated crystals are filtered and washed with cold ethyl acetate or diethyl ether. Yield: 8.5 g (63%). MPT.: 148–150° C.; Mass: reported: [319], found: $[M+H]^+320, [M+Na]^+342, [2M+H]^+639$;

$^1$H-NMR (250 MHz, DMSO-d6): δ [ppm]=8.18 (7H, m, aryl-H); 3.86 (3H, s, OCH$_3$); 3.75 (3H, s, aryl-N—CH$_3$); 3.26 (4H, s, aryl-CH$_2$—CH$_2$—).

e) 2-[2-(4-Cyanophenyl)-ethyl]-1-methyl-benzimidazole-5-yl-carboxylic acid 5.0 g of 2-[2-(4-Cyanophenyl)-ethyl]-1-methyl-benzimidazole-5-yl-carboxylic acid-methyl ester (15.7 mmol) are dissolved in 50 ml of methanol, treated with 20 ml of an aqueous sodium hydroxide solution(1 N) and boiled under reflux for 0.5 hours. It is then treated with 20 ml of an aqueous solution of hydrochloric acid (1 N) and diluted with water. The precipitated crystals are filtered off, and washed with water, acetone and ether. The raw product obtained is re-crystallized from dimethyl formamide. Yield: 4.5 g (94%); MPt.: >220° C.

f) 2-[2-(4-Cyanophenyl)-ethyl]-1-methyl-benzimidazole-5-yl-carboxylic acid-[4-(3-phenyl-allyl)-piperazinyl]-amide 0.4 g of 2-[2-(4-Cyanophenyl)-ethyl]-1-methyl-benzimidazole-5-yl-carboxylic acid (1.3 mmol), 4-(3-phenyl-allyl)-piperazine (0.26 g, 1.3 mmol) and 0.4 ml of triethylamine are dissolved in 8 ml of dimethylformamide. 0.54 g of O-(Benzotriazole-1-yl)-N,N,N',N'-tetramethyluronium-tetrafluoroborate (=TBTU; 1.7 mmol) are added and stirred for 24 h at room temperature. After diluting with 20 ml of ethyl acetate, it is washed with saturated, aqueous sodium bicarbonate solution and with water, and dried over sodium sulphate. The solvent is boiled down and the product purified chromatographically (silica gel; gradient; acetic ester/methanol 100% in 60% acetic ester). Yield: 0.52 g (80%); yellow oil.

g) 2-[2-(4-Amidinophenyl)-ethyl]-1-methyl-benzimidazol-5-yl-carboxylic acid-[4-(3-phenyl-allyl)-piperazinyl]-amid-hydrochlorid:

0.14 g of 2-[2-(4-Cyanophenyl)-ethyl]-1-methyl-benzimidazole-5-yl-carboxylic acid-[4-(3-phenyl-allyl)-piperazinyl]-amide (0.2 mmol) are added to a cooled, saturated at 0° C. ethanolic solution of HCl. Stirring is continued until complete solution of the separated material and the temperature held at 0–5° C. for about 12 hours. The ethanol is distilled off at a maximum temperature of 40° C. and the residue dissolved in 30 ml of an ethanolic ammonia solution saturated at 0° C. Stirring is carried on for 1 hour at room temperature and 2 hours at 40–50° C., treated with 10 ml of the previously described ammonia solution, boiled under reflux for 1 hour and allowed to stand for 12 hours at room temperature. The precipitated inorganic salts are filtered off, the filtrate is reduced to half its volume and then diluted with 50 ml of acetone. The precipitated crystals are filtered off and washed with acetone. Yield: 0.15 g (25%); MPt.: >250° C.;

$^1$H-NMR (250 MHz, DMSO-d6): δ [ppm]=9.25; 8.86 (4H, 2 s, $NH_2$—C=$NH_2^+$); 7.81–7.13 (12H, m, aryl-H); 6.60–6.17 (2H, m, —CH=CH—); 3.67 (3H, s, NH—$CH_3$—); 3.61–2.98 (14H, m/s, O=C—$CH_2$; aryl-$CH_2$—$CH_2$—, piperazin-$CH_2$—, N—$CH_2$—CH=CH—).

EXAMPLES 2 TO 14

The following compounds of Examples 2 to 14 are prepared in an analogous manner to that of the description of Example 1, with the corresponding amines (Stage f). The amine required for the preparation of the compound of Example 6 can be obtained in accordance with the German publication DE 2701 794. The amines required for the preparation of the compounds of the Examples 7 and 12 can be obtained in accordance with the German publication DE 32 35 565.

2 [2-(4-Amidinophenyl)-ethyl]-1-methyl-benzimidazole-5-yl-carboxylic acid-[4-(2-nitro-4-trifluoromethyl-phenyl)-piperazinyl]-amide-dihydrochloride, MPt.: 216° C.

3 [2-(4-Amidinophenyl)-ethyl]-1-methyl-benzimidazole-5-yl-carboxylic acid-[(2-cyclohexyl-ethyl)-piperazinyl]-amide-dihydrochloride, MPt.: 170° C. (Decomp.)

4 [2-(4-Amidinophenyl)-ethyl]-1-methyl-benzimidazole-5-yl-carboxylic acid-[4-(5-benzyl-2,4-dioxo-oxazolidine-3-yl)-piperidinyl]-amide-hydrochloride, MPt: 196° C.

5 [2-(4-Amidinophenyl)-ethyl]-1-methyl-benzimidazole-5-yl-carboxylic acid-{4-[2-benzoylamino-(2,3-dihydro-benzo[1,4]dioxine)]-piperydinyl}-amide-hydrochlorid, MPt.: 140° C. (decomp.)

6 [2-(4-Amidinophenyl)-ethyl]-1-methyl-benzimidazole-5-yl-carboxylic acid-[4-(2-oxo-3-phenyl-imidazolidine-1-yl)-piperidinyl]-amide-hydrochloride, MPt.: 200° C.

7 [2-(4-Amidinophenyl)-ethyl]-1-methyl-benzimidazole-5-yl-carboxylic acid-[4-(2,4-dioxo-1-oxa-3-aza-spiro[4,4]non-3-yl)-piperidinyl]-amide-hydrochloride, MPt.: >250° C.

8 [2-(4-Amidinophenyl)-ethyl]-1-methyl-benzimidazole-5-yl-carboxylic acid-[4-(4-fluorobenzamido)-piperazinyl]-amide-hydrochloride, MPt.: 248° C. (Decomp.)

9 [2-(4-Amidinophenyl)-ethyl]-1-methyl-benzimidazole-5-yl-carboxylic acid-[4-(4-nitrophenyl)-piperazinyl]-amide-dihydrochloride, MPt.: 203° C.

10 [2-(4-Amidinophenyl)-ethyl]-1-methyl-benzimidazole-5-yl-carboxylic acid-[4-(2-pyridylamido)-piperidinyl]-amide-dihydrochloride, MPt.: 155° C. (Decomp.)

11 [2-(4-Amidinophenyl)-ethyl]-1-methyl-benzimidazole-5-yl-carboxylic acid-[4-(3-butyl-ureido)-piperidinyl]-amide-hydrochloride 12 [2-(4-Amidinophenyl)-ethyl]-1-methyl-benzimidazole-5-yl-carboxylic acid-[4-(2,4-dioxo-5-propyl-oxazolidine-3-yl)-piperidinyl]-amide-hydrochloride 13 [2-(4-Amidinophenyl)-ethyl]-1-methyl-benzimidazole-5-yl-carboxylic acid-(4-benzamido-piperidinyl)-amide-hydrochloride 14 [2-(4-Amidinophenyl)-ethyl]-1-methyl-benzimidazole-5-yl-carboxylic acid-{4-[3-(2,3-dichloro-phenyl)-ureido]-piperidinyl}-amide-hydrochloride

EXAMPLE 15

2-[2-(4-Aminomethylphenyl)-ethyl]-1-methyl-benzimidazole-5-yl-carboxylic acid-(4-benzamido-piperidinyl)-amide

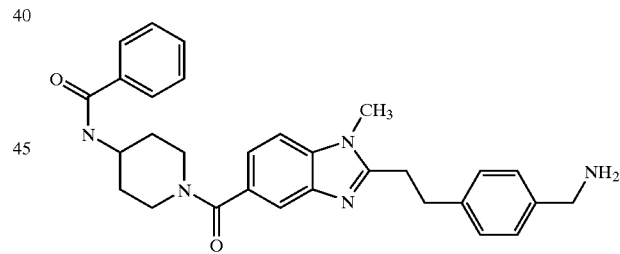

a) 2-[2-(4-Cyanophenyl)-ethyl]-1-methyl-benzimidazole-5-yl-carboxylic acid-(4-benzamido-piperidinyl)-amide:

The synthesis is carried out by starting from 2-[2-(4-Cyanophenyl)-ethyl]-1-methyl-benzimidazole-5-yl-carboxylic acid and by reacting this with 4-benzamidopiperidine in an analogous manner to that of Example 1, stage f.

b) 2-[2-(4-Aminomethyl-phenyl)-ethyl]-1-methyl-benzimidazole-5-yl-carboxylic acid-(4-benzamido-piperidinyl)-amide:

2.0 g (4.1 mmol) 2-[2-(4-Cyanophenyl)-ethyl]-1-methyl-benzimidazole-5-yl-carboxylic acid-(4-benzamido-piperidinyl)-amide are hydrogenated in 30 ml of methanol in the presence of about 2 g of methanol-moist Raney Nickel at room temperature and standard pressure. The catalyst is filtered off and washed with methanol, and the solvent is distilled off under vacuum. The residue is hydrogenated over silica gel (acetic ester:methanol:ammonia, 80:20:1) and then chromatographed over an RP-18 column (gradient acetonitrile:water: 0–2 min. 90% water over 11 min. of 90 to 5% water, 5 min. 5% water). Yield: 0.4 g (20%); MPt.: 165–167° C., $^1$H-NMR (250 MHz, CDCl$_3$, TMS=0 ppm): δ [ppm]= 7.80–7.12 (12H, m, aryl-H); 6.14 (1H, d, J=6.5 Hz, NH—CH); 4.60 (2H, s, wide, NH$_2$); 4.29 (1H, m, piperidine-CH—); 3.85 (2H, s, phenyl-CH$_2$—N); 3.58 (3H, s, aryl-N—CH$_3$); 3.19 (4H, s, aryl-CH$_2$—CH$_2$—); 3.38–1.98 (8H, m, piperidine-CH$_2$—).

EXAMPLE 16

2-[2-(4-Benzoylamidinophenyl)-ethyl]-1-methyl-benzimidazole-5-yl-carboxylic acid-(4-benzamidopiperidinyl)-amide

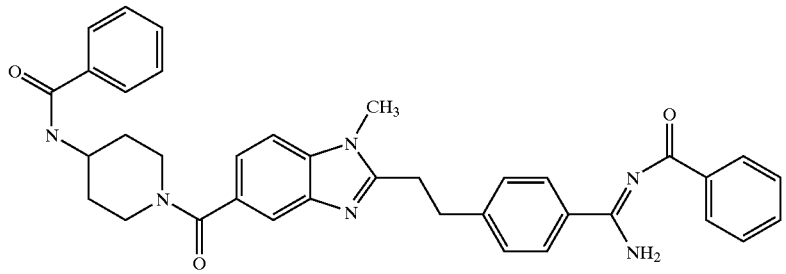

a) 2-[2-(4-Amidinophenyl)-ethyl]-1-methyl-benzimidazole-5-yl-carboxylic acid-(4-benzamido-piperidinyl)-amide:

The synthesis, starting with 2-[2-(4-Cyanophenyl)-ethyl]-1-methyl-benzimidazole-5-yl-carboxylic acid, follows in an analogous manner to that of Example 1, stage g.

b) 2-[2-(4-Benzoylamidinomethyl-phenyl)-ethyl]-1-methyl-benzimidazole-5-yl-carboxylic acid-(4-benzamido-piperidinyl)-amide:

1.0 g (2 mmol) of 2-[2-(4-Amidinophenyl)-ethyl]-1-methyl-benzimidazole-5-yl-carboxylic acid-(4-benzamido-piperidinyl)-amide and 3.2 ml Triethylamine (23 mmol) are dissolved in 10 ml of dimethyl formamide. The mixture is cooled down to 0° C. and 0.418 ml of benzoyl chloride (3.6 mmol) are slowly added dropwise. After 2 hours 20 ml of water are added to the mixture, and the aqueous phase is extracted with 20 ml of acetic ester. The organic phase is again washed with water and dried over sodium sulphate. The solvent is distilled off under vacuum. The residue is chromatographed over silica gel with acetic ester, and the oily product is triturated with petroleum ether. The precipate is filtered and washed with petroleum ether. Yield: 0.160 g (15%); MPt: 150–154° C.;

$^1$H-NMR (250 MHz, DMSO-d6): δ [ppm]=8.43 (1H, d, J=7.5 Hz, NH—CH); 8.37–7.28 (19H, m, aryl-H, NH$_2$); 3.79 (3H, s, N—CH$_3$); 3.30 (4H, 2 m, aryl-CH$_2$—CH$_2$—); 4.26–1.32 (9H, m, piperidine-CH$_2$—CH).

EXAMPLE 17

2-[2-(4-Amidinophenyl)-ethyl]-1-(3-ethoxy-propyl)-benzimidazole-5-yl-carboxylic acid-[4-(2-phenyl-ethyl)-piperazinyl]-amide-dihydrochloride

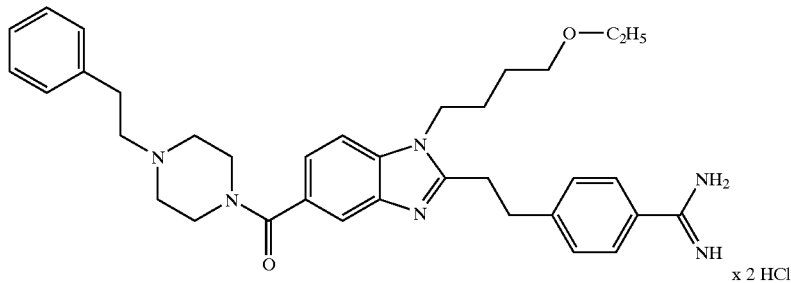

a) 4-(3-ethoxy-propyl)-3-nitrobenzoic acid:

90 ml (0.74 mmol) of 3-ethoxy-propylamine are dissolved in 90 ml of water, and 20 g of 4-chloro-3-nitro-benzoic acid (100 mmol) are added to it portionwise. The mixture is stirred for 24 hours at 70° C. After cooling, it is acidified with acetic acid. The crystals formed are filtered off, washed with cold water and dried. Yield: 20 g (75%).

The other intermediary stages are synthesised with reference to the procedure given in Example 1 with the 4-(2-phenyl-ethyl)-piperizine (Stage f). From 0.5 g 2-[2-(4- cyanophenyl)-ethyl]-1-(3-ethoxy-propyl)-benzimidazole-5-yl-carboxylic acid-[4-(2-phenyl-ethyl)-piperazinyl]-amide, 0.32 mg (62%) of crystals are obtained.

$^1$H-NMR (250 MHz, DMSO-d6): δ [ppm]=9.30; 9.05 (4H, 2 s, NH$_2$—C=NH$_2$$^+$); 7.81–6.98 (12H, m, aryl-H); 4.25–1.78 (24H, m, 2×(aryl-CH$_2$—CH$_2$—), N—(CH$_2$)$_3$—O—CH$_2$), -piperazine-CH$_2$); 1.07 (3H, t, J=6.7 Hz, —O—CH$_2$<u>CH$_3$</u>.

EXAMPLES 18 TO 23

The compounds of the Examples 18 to 23 are produced in an analogous manner to that described in Example 17, with the corresponding amines (Stage f). The amine required for the production of the compound of Example 22 can be obtained in accordance with the German publication DE 32 35 565.

18 2-[2-(4-Amidinophenyl)-ethyl]-1-(3-ethoxy-propyl)-benzimidazole-5-yl-carboxylic acid-(4-benzamido-piperidinyl)-amide-hydrochloride, MPt.: >250° C.

19 2-[2-(4-Amidinophenyl)-ethyl]-1-(3-ethoxy-propyl)-benzimidazole-5-yl-carboxylic acid-[4-(3-phenyl-allyl)-piperazinyl]-amide-hydrochloride, MPt.: 238° C. (Decomp.)

20 2-[2-(4-Amidinophenyl)-ethyl]-1-(3-ethoxy-propyl)-benzimidazol-5-yl-carbons äure-[4-(3-phenyl-ureido)-piperidinyl]-amid-dihydro chlorid, Schmp.: 235° C. (Decomp.)

21 2-[2-(4-Amidinophenyl)-ethyl]-1-(3-ethoxy-propyl)-benzimidazol-5-yl-carboxylic acid-{4-[2-benzoylamino-(2,3-dihydro-benzo[1,4]dioxin)]-piperydinyl}-amide-dihydrochloride, MPt.: 230° C. (Decomp.)

22 2-[2-(4-Amidinophenyl)-ethyl]-1-(3-ethoxy-propyl)-benzimidazole-5-yl-carboxylic acid-[4-(5-benzyl-2,4-dioxo-oxazolidine-3-yl)-piperidinyl]-amide-dihydrochloride, MPt.: 185° C. (Decomp.)

23 2-[2-(4-Amidinophenyl)-ethyl]-1-(3-ethoxy-propyl)-benzimidazole-5-yl-carboxylic acid-[(2-cyclohexyl-ethyl)-piperazinyl]-amide-trihydrochloride, MPt.: 240° C. (Decomp.)

EXAMPLE 24

[2-(4-Amidinophenyl)-ethyl-1-methyl-benzimidazole-5-yl-carboxylic acid-{4-[3-(2,3-dichloro-phenyl)-ureido]-piperidinyl}-amide-hydrochloride

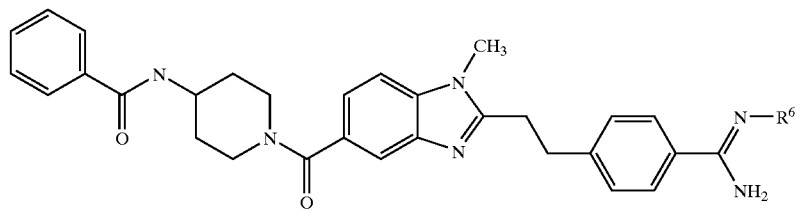

(IIA)

a) 1-(2,3-Dichloro-phenyl)-3-piperidine-4-yl-urea:

0.66 g (3.3 mmol) of 4-Amino-piperidine-1-carboxylic acid tert-butyl ester are dissolved in 30 ml of dichloroethane, treated with 3.3 mmol of 2,3-dichlorophenyl isocyanate and stirred at room temperature for 3 hours. In order to complete the reaction, it is heated at 50° C. for 4 hours. It is then treated with 2.5 ml of trifluoroacetic acid at room temperature and then allowed to stand for 24 hours. The solvent is distilled off under vacuum, and the product is immediately reacted further under b). Yield of a yellowish solid: 1.3 g, HPLC-MS, purity: 98% (reported: 287; found: [M+H]+288; column: Waters XTerra, C18MS, 4.6×50, 3.51 µm; solvent A: Water (0.1% TFA), solvent B: Acetonitrile (0.1% TFA), gradient: 95% A to 98% B in 5 min., flow rate: 1 ml/min.

b) Linkage in an analogous manner with the benzimidazole building block as in Example 1 (Stage f)

EXAMPLES 25 TO 63

The compounds of the Examples 25 to 63 are prepared in an analogous manner as described in Example 24, using the corresponding amines (Stage f).

| | [M + H]⁺ | Ret. Time* [min.] |
|---|---|---|
| 25 4-(2-{1-Methyl-5-[4-(3-m-tolyl-ureido)-piperidine-1-carbonyl]-1H-benzimidazole-2-yl}-ethyl)-benzamidine | [538] | 3.18 |
| 26 4-[2-(5-{4-[3-(3-Fluoro-phenyl)-ureido]-piperidine-1-carbonyl}-1-methyl-1H-benzimidazole-2-yl)-ethyl]-benzamidine | [542] | 3.17 |
| 27 4-[2-(5-{4-[3-(2-Fluoro-phenyl)-ureido]-piperidine-1-carbonyl}-1-methyl-1H-benzimidazole-2-yl)-ethyl]-benzamidine | [542] | 3.03 |
| 28 4-[2-(5-{4-[3-(3-Methoxy-phenyl)-ureido]-piperidine-1-carbonyl}-1-methyl-1H-benzimidazole-2-yl)-ethyl]-benzamidine | [554] | 3.02 |
| 29 4-[2-(5-{4-[3-(2-Chloro-phenyl)-ureido]-piperidine-1-carbonyl}-1-methyl-1H-benzimidazole-2-yl)-ethyl]-benzamidine | [558] | 3.21 |
| 30 4-[2-(5-{4-[3-(2-Methoxy-phenyl)-ureido]-piperidine-1-carbonyl}-1-methyl-1H-benzimidazole-2-yl)-ethyl]-benzamidine | [554] | 4.9** |
| 31 4-[2-(5-{4-[3-(4-Chloro-phenyl)-ureido]-piperidine-1-carbonyl}-1-methyl-1H-benzimidazole-2-yl)-ethyl]-benzamidine | [558] | 3.33 |
| 32 4-[2-(1-Methyl-5-{4-[3-(3-trifluoromethyl-phenyl)-ureido]-piperidine-1-carbonyl}-1H-benzimidazole-2-yl)-ethyl]-benzamidine | [592] | 3.48 |
| 33 4-[2-(5-{4-[3-(2,4-Difluoro-phenyl)-ureido]-piperidine-1-carbonyl}-1-methyl-1H-benzimidazole-2-yl)-ethyl]-benzamidine | [560] | 3.12 |
| 34 4-[2-{1-Methyl-5-[4-(3-naphthalen-1-yl-ureido)-piperidine-1-carbonyl]-1H-benzimidazole-2-yl}-ethyl)-benzamidine | [574] | 3.26 |
| 35 4-[2-(5-{4-[3-(2,4-Dichloro-phenyl)-ureido]-piperidine-1-carbonyl}-1-methyl-1H-benzimidazole-2-yl)-ethyl]-benzamidine | [592] | 5.66** |
| 36 4-[2-{1-Methyl-5-[4-(3-naphthalen-2-yl-ureido)-piperidine-1-carbonyl]-1H-benzimidazole-2-yl}-ethyl)-benzamidine | [574] | 5.49** |
| 37 4-[2-(5-{4-[3-(2-Bromo-phenyl)-ureido]-piperidine-1-carbonyl}-1-methyl-1H-benzimidazole-2-yl)-ethyl]-benzamidine | [602] | 3.22 |
| 38 4-[2-(5-{4-[3-(2,6-Difluoro-phenyl)-ureido]-piperidine-1-carbonyl}-1-methyl-1H-benzimidazole-2-yl)-ethyl]-benzamidine | [560] | 4.45** |
| 39 4-[2-(5-{4-[3-(4-Bromo-phenyl)-ureido]-piperidine-1-carbonyl}-1-methyl-1H-benzimidazole-2-yl)-ethyl]-benzamidine | [602] | 3.37 |
| 40 4-(2-{5-[4-(3-Cyclohexyl-ureido)-piperidine-1-carbonyl]-1-methyl-1H-benzimidazole-2-yl}-ethyl)-benzamidine | [530] | 4.76** |
| 41 4-[2-(1-Methyl-5-{4-[3-(4-trifluoromethyl-phenyl)-ureido]-piperidine-1-carbonyl}-1H-benzimidazole-2-yl)-ethyl]-benzamidine | [592] | 5.67 |
| 42 4-[2-(5-{4-[3-(4-Fluoro-phenyl)-ureido]-piperidine-1-carbonyl}-1-methyl-1H-benzimidazole-2-yl)-ethyl]-benzamidine | [542] | 3.06 |
| 43 4-[2-(5-{4-[3-(3-Bromo-phenyl)-ureido]-piperidine-1-carbonyl}-1-methyl-1H-benzimidazole-2-yl)-ethyl]-benzamidine | | |
| 44 2-[2-(4-Amidinophenyl)-ethyl]-1-methyl-benzimidazole-5-yl-carboxylic acid-[4-(3-chloro)-benzamidopiperidinyl)-amide | | |
| 45 2-[2-(4-Amidinophenyl)-ethyl]-1-methyl-benzimidazole-5-yl-carboxylic acid-[4-(3-bromo)-benzamidopiperidinyl)-amide | | |
| 46 2-[2-(4-Amidinophenyl)-ethyl]-1-methyl-benzimidazole-5-yl-carboxylic acid-[4-(2-hydroxy)-benzamidopiperidinyl)-amide | | |
| 47 2-[2-(4-Amidinophenyl)-ethyl]-1-methyl-benzimidazole-5-yl-carboxylic acid-[4-(2-difluoromethylsulfanyl)-benzamidopiperidinyl)-amide | | |
| 48 2-[2-(4-Amidinophenyl)-ethyl]-1-methyl-benzimidazole-5-yl-carboxylic acid-[4-(3-difluoromethylsulfanyl)-benzamidopiperidinyl)-amide | | |
| 49 2-[2-(4-Amidinophenyl)-ethyl]-1-methyl-benzimidazole-5-yl-carboxylic acid-[4-(2,3-dichloro)-benzamidopiperidinyl)-amide | | |

| | [M + H]⁺ | Ret. Time*<br>[min.] |
|---|---|---|
| 50 2-[2-(4-Amidinophenyl)-ethyl]-1-methyl-benzimidazole-5-yl-carboxylic acid-[4-(2-methoxy)-benzamidopiperidinyl)-amide | | |
| 51 2-[2-(4-Amidinophenyl)-ethyl]-1-methyl-benzimidazole-5-yl-carboxylic acid-[4-(2-bromo)-benzamidopiperidinyl)-amide | | |
| 52 2-[2-(4-Amidinophenyl)-ethyl]-1-methyl-benzimidazole-5-yl-carboxylic acid-[4-(2-chloro)-benzamidopiperidinyl)-amide | | |
| 53 2-[2-(4-Amidinophenyl)-ethyl]-1-methyl-benzimidazole-5-yl-carbooxylic acid-[4-(N-methyl)benzamidopiperidinyl]-amide | | |
| 54 2-[2-(4-Amidinophenyl)-ethyl]-1-methyl-benzimidazole-5-yl-carboxylic acid-(4-anilinopiperidinyl)-amide | | |
| 55 2-[2-(4-Amidinophenyl)-ethyl]-1-methyl-benzimidazole-5-yl-carboxylic acid-{4-[3-(2,3-dichloro)-phenyl-1-methyl-ureido]piperidinyl)-amide | | |
| 56 2-[2-(4-Amidinophenyl)-ethyl]-1-methyl-benzimidazole-5-yl-carboxylic acid-{4-[3-(3-acetyl)-phenylureido]piperidinyl}-amide | | |
| 57 2-[2-(4-Amidinophenyl)-ethyl]-1-methyl-benzimidazole-5-yl-carboxylic acid-{4-[3-(3-methoxycarbonyl)phenylureido]piperidinyl}-amide | | |
| 58 2-[2-(4-Amidinophenyl)-ethyl]-1-methyl-benzimidazole-5-yl-carboxylic acid-{4-[3-(3-methylsulfanyl)phenylureido]piperidinyl}-amide | | |
| 59 2-[2-(4-Amidinophenyl)-ethyl]-1-methyl-benzimidazole-5-yl-carboxylic acid-{4-[3-(3-iodo)-phenylureido]piperidinyl}-amide | | |
| 60 2-[2-(4-Amidinophenyl)-ethyl]-1-methyl-benzimidazole-5-yl-carboxylic acid-{4-[3-(3-chloro)-phenylureido]piperidinyl}-amide | | |
| 61 2-[2-(4-Amidinophenyl)-ethyl]-1-methyl-benzimidazole-5-yl-carboxylic acid-{4-[3-(3-methoxycarbonyl)-phenyl-1-methyl-ureido]piperidinyl)-amide | | |

*Column: Waters XTerra, C18MS, 4.6 × 50, 3.5 μm; solvent A: Water (0.1% TFA), solvent B: Acetonitrile (0.1% TFA), gradient: 95% A to 98% B in 5 min., flow rate: 1 ml/min.
**Column: Waters XTerra, C18MS, 4.6 × 50, 3.5 μm; solvent A: Water (0.1% TFA), solvent B: Acetonitrile (0.1% TFA), gradient: 95% A to 95% B in 9 min., flow rate: 1 ml/min.

EXAMPLE 62

[2-(4-Amidinophenyl)-ethyl]-1-methyl-benzimidazole-5-yl-carboxylic acid-{4-[3-(3-carboxyphenyl)-ureido]-piperidinyl}-amide

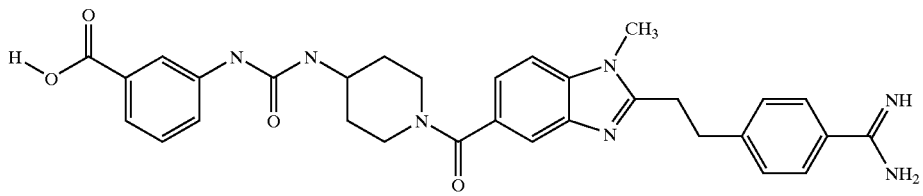

0.3 g (0.48 mmol) of 2-[2-(4-Amidinophenyl)-ethyl]-1-methyl-benzimidazole-5-yl-carboxylic acid-{4-[3-(3-methoxycarbonyl)phenylureido]piperidinyl}-amide (Example 57) are dissolved in 5 ml of methanol and treated with 1.2 ml of 2N caustic soda solution and allowed to stand for 5 hours at room temperature. It is then treated with 0.1 ml of acetic acid and diluted with water. The precipitate is filtered off under suction and washed with water. 0.2 g of a white solid is obtained. MPt: 231–235° C.

EXAMPLES 63–201

The compounds listed in the following Tables I to IV are prepared in an analogous manner to that described in the previous Example.

TABLE I

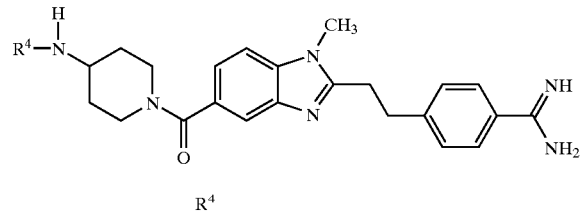

| | R⁴ |
|---|---|
| 63 | 3-Chloro-6-propylphosponyloxybenzoyl |
| 64 | 2,5-Dichlorobenzoyl |
| 65 | 2,3-Dichlorophenyl |
| 66 | Naphth-1-yl |
| 67 | 2,3-Dichlorobenzoyl |

TABLE II

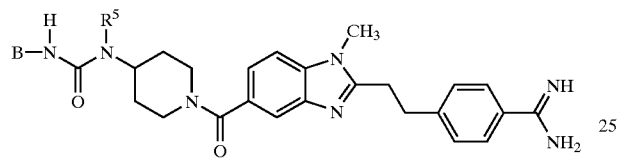

| | B | R⁵ |
|---|---|---|
| 68 | 3-Mehoxycarbonylphenyl | Methyl |
| 69 | 4-Chlorophenyl | H |
| 70 | 4-Chlorophenyl | 4-Methanesulfonyl-benzyl |
| 71 | 4-Chlorophenyl | Pyrid-2-ylmethyl |
| 72 | 4-Chlorophenyl | 4-Bromobenzyl |
| 73 | 4-Chlorophenyl | 4-Benzenesulfonamide-methyl |
| 74 | Phenyl | H |
| 75 | Phenyl | 4-Methanesulfonylbenzyl |
| 76 | 4-Chlorophenyl | Prop-2-in-1-yl |
| 77 | 4-Cyanophenyl | Pyrid-2-ylmethyl |
| 78 | 4-Chlorophenyl | 3-Trifluoromethoxybenzyl |
| 79 | 4-Chlorophenyl | 1-Naphthalin-1-ylmethyl |
| 80 | Phenyl | Pyrid-2-ylmethyl |
| 81 | Phenyl | 4-Bromobenzyl |
| 82 | 4-Chlorophenyl | 2-(Pyrrolidin-1-yl)-ethyl |
| 83 | 4-Chorophenyl | Pyrid-3-ylmethyl |
| 84 | Phenyl | 3-Trifluoromethoxybenzyl |
| 85 | 4-Chlorophenyl | 2,2,2-Trifluoroethyl |
| 86 | 4-Chlorophenyl | Methyl |
| 87 | Phenyl | Naphthalin-1-ylmethyl |
| 88 | 1,1'-Biphenyl-4-yl | 3-(Morpholino-1-yl)-propyl |
| 89 | 4-Chlorophenyl | 2-(Thien-2-yl)-ethyl |
| 90 | 4-Chlorophenyl | 3,5-Bis-trifluoromethyl-benzyl |
| 91 | Phenyl | 3,5-Bis-trifluoromethyl-benzyl |
| 92 | 4-Chlorophenyl | Pyrid-4-ylmethyl |
| 93 | 4-Chlorophenyl | (4-Benzenesulfonamidyl)-methyl |
| 94 | Phenyl | (4-Benzenesulfonamidyl)-methyl |
| 95 | 4-Chlorophenyl | Cyclopropyl-methyl |
| 96 | 4-Cyanophenyl | 4-Bromobenzyl |
| 97 | 1,1'-Biphenyl-4-yl | Pyrid-3-ylmethyl |
| 98 | 4-Cyanophenyl | (4-Benzene-sulfonamidyl)methyl |
| 99 | 4-Chlorophenyl | 3-Ethoxypropyl |
| 100 | 4-Chlorophenyl | 3-(Morpholino-1-yl)-propyl |
| 101 | Phenyl | 2,2,2-Trifluoroethyl |
| 102 | 1,1'-Biphenyl-4-yl | 4-Bromobenzyl |
| 103 | 4-Cyanophenyl | 4-Methanesulfonyl-benzyl |
| 104 | 4-Cyanophenyl | 3,5-Bis-trifluoromethyl-benzyl |
| 105 | Propionyl | Naphthalin-1-ylmethyl |
| 106 | Phenyl | Pyrid-4-ylmethyl |
| 107 | Phenyl | Prop-2-in-1-yl |

TABLE II-continued

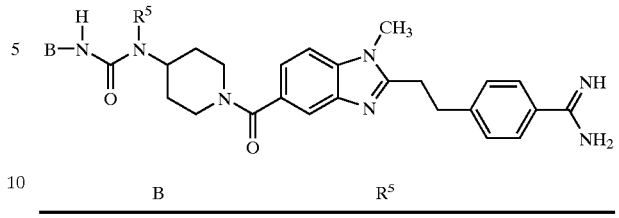

| | B | R⁵ |
|---|---|---|
| 108 | Propionyl | H |
| 109 | Phenyl | 2-(Thien-2-yl)-ethyl |
| 110 | 4-Cyanophenyl | Pyrid-4-ylmethyl |
| 111 | 4-Cyanophenyl | 3-Trifluoromethoxy-benzyl |
| 112 | Phenyl | Pyrid-3-ylmethyl |
| 113 | Phenyl | Methyl |
| 114 | 4-Cyanophenyl | 3-(Morpholino-1-yl)-propyl |
| 115 | 4-Chlorophenyl | 3-(Pyrrolidin-2-on-1-yl)-propyl |
| 116 | Phenyl | Cyclopropyl-methyl |
| 117 | 4-Cyanophenyl | Naphthalin-1-ylmethyl |
| 118 | 1,1'-Biphenyl-4-yl | 3,5-Bis-trifluoromethyl-benzyl |
| 119 | 4-Cyanophenyl | 2,2,2-Trifluorethyl |
| 120 | 4-Cyanophenyl | 2-(4-Benzenesulfonamidyl)-ethyl |
| 121 | Phenyl | 2-(4-Benzenesulfonamidyl)-ethyl |
| 122 | Phenyl | 3-(Pyrrolidin-2-on-1-yl)-propyl |
| 123 | 4-Cyanophenyl | Cyclopropyl-methyl- |
| 124 | Phenyl | 3-(Morpholino-1-yl)-propyl |
| 125 | 4-Cyanophenyl | Pyrid-3-ylmethyl- |
| 126 | Phenyl | 3-Ethoxypropyl |
| 127 | 4-Cyanophenyl | 2-(Pyrrolidin-1-yl)-ethyl |
| 128 | 1,1'-Biphenyl-4-yl | 2-(Thien-2-yl)-ethyl |
| 129 | 4-Cyanophenyl | Methyl |
| 130 | Propionyl | 4-Bromobenzyl |
| 131 | 1,1'-Biphenyl-4-yl | 3-Ethoxypropyl |
| 132 | 4-Cyanophenyl | 3-(Pyrrolidin-2-on-1-yl)-propyl |
| 133 | 4-Cyanophenyl | H |
| 134 | Propionyl | 3-Trifluoromethoxy-benzyl- |
| 135 | Phenyl | 2-(Pyrrolidin-1-yl)-ethyl- |
| 136 | 1,1'-Biphenyl-4-yl | 3-(Pyrrolidin-2-on-1-yl)-propyl |
| 137 | 1,1'-Biphenyl-4-yl | 2-(Pyrrolidin-1-yl)-ethyl |
| 138 | 1,1'-Biphenyl-4-yl | 3-Trifluoromethoxy-benzyl |
| 139 | Propionyl | 4-Methanesulfonyl-benzyl |
| 140 | 4-Cyanophenyl | 3-Ethoxypropyl |
| 141 | 1,1'-Biphenyl-4-yl | Pyrid-4-ylmethyl |
| 142 | Propionyl | 3,5-Bis-trifluoromethyl-benzyl |
| 143 | Propionyl | Cyclopropyl-methyl |
| 144 | Propionyl | Prop-2-in-1-yl |
| 145 | 1,1'-Biphenyl-4-yl | 2-(4-Benzenesulfonamidyl)-ethyl |
| 146 | Propionyl | (4-Benzenesulfonamidyl)-methyl |
| 147 | 1,1'-Biphenyl-4-yl | Methyl |
| 148 | 1,1'-Biphenyl-4-yl | 4-Methanesulfonyl-benzyl |
| 149 | 1,1'-Biphenyl-4-yl | H |
| 150 | 1,1'-Biphenyl-4-yl | (4-Benzenesulfonamidyl)-methyl |
| 151 | Propionyl | 2-(Thien-2-yl)-ethyl |
| 152 | Propionyl | Pyrid-4-ylmethyl |
| 153 | Propionyl | 2-(Pyrrolidin-1-yl)-ethyl |
| 154 | Propionyl | Methyl |
| 155 | Propionyl | Pyrid-2-ylmethyl |
| 156 | 1,1'-Biphenyl-4-yl | Pyrid-2-ylmethyl |
| 157 | 1,1'-Biphenyl-4-yl | 2,2,2-Trifluoroethyl- |
| 158 | 1,1'-Biphenyl-4-yl | Prop-2-in-1-yl |
| 159 | Propionyl | Pyrid-3-ylmethyl |
| 160 | Propionyl | 2-(4-Benzenesulfonamidyl)-ethyl |
| 161 | Propionyl | 3-Ethoxypropyl |
| 162 | Propionyl | 3-(Pyrrolidin-2-on-1-yl)-propyl |

TABLE II-continued

| | B | R⁵ |
|---|---|---|
| 163 | Propionyl | 3-(Morpholino-1-yl)-propyl |
| 164 | Benzenesulfonyl- | H |
| 165 | Propionyl | 2,2,2-Trifluoroethyl |

TABLE III

| | R⁴ | R⁵ |
|---|---|---|
| 166 | (E)-2-Phenyl-ethen-1-sulfonyl | Methyl |
| 167 | (E)-2-Phenyl-ethen-1-sulfonyl | H |
| 168 | Butan-1-sulfonyl | Methyl |
| 169 | Naphthalene-1-ylsulfonyl | Methyl |
| 170 | 3-Chloro-2-methyl-benzene-1-sulfonyl | Methyl |
| 171 | 2,3-Dichlorobenzene-1-sulfonyl | Methyl |
| 172 | 3-Nitrobenzene-1-sulfonyl | H |
| 173 | Butane-1-sulfonyl | H |
| 174 | 3-Chlorobenzene-1-sulfonyl | Methyl |
| 175 | 3-Bromobenzene-1-sulfonyl | Methyl |
| 176 | Naphthalene-1-ylsulfonyl | H |
| 177 | 5-Dimethylamino-naphthalene-1-ylsulfonyl | Methyl |
| 178 | Benzenesulfonyl | Methyl |
| 179 | 5-Dimethylamino-naphthalene-1-ylsulfonyl | H |
| 180 | 3-Chloro-2-methyl-benzene-1-sulfonyl | H |
| 181 | 2,5-Dichlorobenzene-1-sulfonyl | Methyl |
| 182 | 3-Nitrobenzene-1-sulfonyl | Methyl |
| 183 | 3-Chlorobenzene-1-sulfonyl | H |
| 184 | 3-Bromobenzene-1-sulfonyl | H |
| 185 | 2,5-Dichlorobenzene-1-sulfonyl | H |
| 186 | 2,3-Dichlorobenzene-1-sulfonyl | H |
| 187 | 3-Trifluoromethylbenzene-1-sulfonyl | Methyl- |
| 188 | 3-Trifluoromethylbenzene-1-sulfonyl | H |
| 189 | 2-(Naphthalene-1-yl)-acetyl | H |

TABLE IV

| | R⁴ |
|---|---|
| 190 | 2-Fluoroanilinocarbonyl |
| 191 | 3-Methoxyanilinocarbonyl |
| 192 | 2-Chloroanilinocarbonyl |
| 193 | 3-Chloroanilinocarbonyl |

TABLE IV-continued

| | R⁴ |
|---|---|
| 194 | 3-Bromoanilinocarbonyl |
| 195 | 2,3-Dichloroanilinocarbonyl |
| 196 | Benzoyl |
| 197 | 3-Chlorobenzoyl |
| 198 | 3-Bromobenzoyl |
| 199 | 3-Iodobenzoyl |
| 200 | 3-Methylsulphonylbenzoyl |
| 201 | 2,3-Dichlorobenzoyl |

The compounds of the invention are notable for their effective trypsin-inhibiting property. The said capacity to inhibit trypsin activity was determined in accordance with the following trial descriptions.

The determinations are carried out in tris-HCl buffer (100 mM), that also contained calcium (5 mM) and heparin (100 mg/ml), at a pH of 7.4. As the standard, rh beta trypsin is used, this is commercially obtainable, for example, from Promega. A suitable substrate is N-p-Gly-Pro-Lys-para-nitroaniline in a concentration of 0.6 mM. The substrate is digested with trypsin, whereby p-nitro-aniline is obtained that can be measured at 405 nm. Normally, an incubation period of 5 minutes and an incubation temperature of 37° C. is chosen. For the enzyme activity, 0.91 U/ml are used. The determination is carriedout in an auto-analyser (Cobas Bio) from the firm Hoffmann LaRoche. The potential inhibitor substances are used in the screening procedure in concentrations of 10 $\mu$M, and the inhibition of the trypsin is given in percentages. At an inhibition in excess of 70%, the $IC_{50}$ is determined (the concentration at which 50% of the enzyme activity is inhibited). After a 5-minute pre-incubation of the potential inhibiting substance, the substrate is added for the start of the reaction, whereby the production of p-nitro-aniline is taken, after 5 minutes, after testing the linearity, as a measure of the enzyme activity.

The following Table V contains the results obtained from in vitro tests of the compounds of the invention having the formula I. The symbols are:

| | |
|---|---|
| +++ | IC50: 0.0001–0.0010 $\mu$M |
| ++ | IC50: 0.0010–0.0200 $\mu$M |
| + | IC50: 0.0200–0.0500 $\mu$M |

TABLE V

| Example | Trypsin-inhibiting property |
|---|---|
| 1 | ++ |
| 2 | ++ |
| 3 | ++ |
| 4 | ++ |
| 5 | ++ |
| 6 | ++ |
| 7 | ++ |
| 8 | ++ |
| 9 | ++ |

TABLE V-continued

| Example | Trypsin-inhibiting property |
|---|---|
| 10 | ++ |
| 11 | ++ |
| 12 | ++ |
| 13 | ++ |
| 14 | +++ |
| 15 | ++ |
| 17 | + |
| 18 | ++ |
| 19 | ++ |
| 20 | ++ |
| 21 | ++ |
| 22 | ++ |
| 23 | ++ |
| 24 | +++ |
| 25 | ++ |
| 26 | ++ |
| 27 | +++ |
| 28 | +++ |
| 29 | +++ |
| 30 | ++ |
| 31 | ++ |
| 32 | ++ |
| 33 | ++ |
| 34 | ++ |
| 35 | ++ |
| 36 | ++ |
| 37 | +++ |
| 38 | ++ |
| 39 | ++ |
| 40 | ++ |
| 41 | ++ |
| 42 | ++ |
| 43 | +++ |
| 44 | +++ |
| 45 | +++ |
| 46 | ++ |
| 49 | ++ |
| 50 | ++ |
| 53 | ++ |
| 55 | ++ |
| 56 | ++ |
| 57 | ++ |
| 58 | +++ |
| 60 | +++ |
| 61 | ++ |
| 62 | ++ |
| 63 | ++ |
| 64 | +++ |
| 65 | ++ |
| 66 | ++ |
| 67 | +++ |
| 68 | + |
| 69 | ++ |
| 70 | ++ |
| 71 | ++ |
| 72 | ++ |
| 73 | ++ |
| 74 | ++ |
| 75 | ++ |
| 76 | ++ |
| 77 | ++ |
| 78 | ++ |
| 79 | ++ |
| 80 | ++ |
| 81 | ++ |
| 82 | ++ |
| 83 | ++ |
| 84 | ++ |
| 85 | ++ |
| 86 | ++ |
| 87 | ++ |
| 88 | ++ |
| 89 | ++ |
| 90 | ++ |
| 91 | ++ |
| 92 | ++ |
| 93 | ++ |
| 94 | ++ |
| 95 | ++ |
| 96 | ++ |
| 97 | ++ |
| 98 | ++ |
| 99 | ++ |
| 100 | ++ |
| 101 | ++ |
| 102 | ++ |
| 103 | ++ |
| 104 | ++ |
| 105 | ++ |
| 106 | ++ |
| 107 | ++ |
| 108 | ++ |
| 109 | ++ |
| 110 | ++ |
| 111 | ++ |
| 112 | ++ |
| 113 | ++ |
| 114 | ++ |
| 115 | ++ |
| 116 | ++ |
| 117 | ++ |
| 118 | ++ |
| 119 | ++ |
| 120 | ++ |
| 121 | ++ |
| 122 | + |
| 123 | + |
| 124 | + |
| 125 | + |
| 126 | + |
| 127 | + |
| 128 | + |
| 129 | + |
| 130 | + |
| 131 | + |
| 132 | + |
| 133 | + |
| 134 | + |
| 135 | + |
| 136 | + |
| 137 | + |
| 138 | + |
| 139 | + |
| 140 | + |
| 141 | + |
| 142 | + |
| 143 | + |
| 144 | + |
| 145 | + |
| 146 | + |
| 147 | + |
| 148 | + |
| 149 | + |
| 166 | ++ |
| 167 | ++ |
| 168 | ++ |
| 169 | ++ |
| 170 | ++ |
| 171 | + |
| 173 | + |
| 189 | ++ |
| 196 | + |

The following Table VI contains the results of the in vitro tests carried out on the pro-drugs of the invention of the formula IIA

TABLE VI

| Prodrug | R⁶ | IC50 [$\mu$M] |
|---|---|---|
| IIA1 | OH | 3.66 |
| IIA2 | OCO-Phenyl | 3.16 |
| IIA3 | OCOO-Methyl | 5.18 |
| IIA4 | O-Methyl | 37.5 |
| IIA5 | COO-Methyl | 0.09 |
| IIA6 | COO-Ethyl | 2.49 |
| IIA7 | COO-n-Propyl | 4.02 |
| IIA8 | COO-n-Pentyl | 5.8 |
| IIA9 | COO-n-Hexyl | 5.62 |
| IIA10 | COO-n-Octyl | 7.91 |
| IIA11 | COO-i-Propyl | 4.39 |
| IIA12 | COO-tert-Butyl | 3.46 |
| IIA13 | COO-2,2,2-Trichloroethyl | 2.53 |
| IIA14 | COO-Benzyl | 0.12 |
| IIA15 | COO-4-Methoxyphenyl | 0.16 |
| IIA16 | COO-4-Methylphenyl | 0.06 |
| IIA17 | CO-Phenyl | 0.36 |
| IIA18 | OCO-Methyl | 4.16 |
| IIA19 | COO—CH(Methyl)—O—CO— | 0.40 |
| IIA20 | CO—CH=CH-(ortho-Acetoxyphenyl) | 0.098 |

The trypsin-inhibitors of the invention can be administered orally, trans-dermally, by inhalation or parenterally. The compounds of the invention comprise the active ingredients in standard forms of administration such, for example, as in compositions that are, substantially, made up of an inert pharmaceutical carrier with an effective dosage of the active ingredient such, for example, as tablets, pills, capsules, wafers, powders, solutions, suspensions, emulsions, syrups, suppositories, transdermal systems, etc. An effective dosage of the compounds of the present invention would be, in the case of an oral form, between 1 and 100, preferably between 1 and 50, especially preferably between 5 and 30 mg/dose; in the case an intra-venous or intramuscular administration, it would be between 0.001 and 50, preferably between 0.1 and 10 mg/dose. For inhalation, the solutions of the invention would suitably contain 0.01 to 1.0, preferably 0.1 to 0.5% of active ingredient. For the inhalative administration, the use of powders is preferred. In addition, it is possible to administer the compounds of the invention in the form of infusion solutions, preferably in a physiological cooking salt solution or nutritional salt solution.

The compounds of the invention may be administered separately or in combination with other active ingredients of the invention, if required, in combination with other pharmacologically active ingredients. Suitable administrative forms are, for example, tablets, capsules, plugs, solutions, juices, emulsions or dispersible powders. Appropriate tablets can, for example, be based on mixtures of this or these active ingredients with known carriers such, for example, as inert diluents such as calcium carbonate, calcium phosphate or lactose, disintegrating agents such, for example, as maize starch or algin acid, binding agents such as starch or gelatine, lubricants such as magnesium stearate or talc, and/or agents for providing a sustained release action such as carboxy-methyl cellulose, cellulose acetate-phthalate, or polyvinyl acetate. The tablets can also consist of several layers.

Appropriately, pills can be prepared by coating tablets, that are prepared analogously as kernels, with, normally, pill-coating materials such, for example, as collidon or varnish, gum arabica, talc, titanium dioxide or sugar. For providing a sustained release action, or to prevent incompatibilities, the kernels can also comprise several layers. Similarly, the pill coating can comprise a number of layers for achieving a depot action, whereby the carrier substances referred to above in connection with the tablets, can be incorporated.

Juices containing the active ingredients of the invention, or combinations of active ingredients, can additionally contain a sweetening agent such as saccharine, cyclamate, glycerine or sugar, as well as a taste-improving substance such, for example, as aroma substances such as vanilla- or orange-extract. They can, in addition, contain suspension-promoting agents or thickeners such as sodium carboxy-methyl cellulose, or wetting agents such, for example, as condensation products of aliphatic alcohols with ethylene oxide, or protective substances such as p-hydroxy-benzoate.

Injectable solutions are usually prepared, for example, with the addition of preserving agents, such as p-hydroxybenzoates, or stabilizers, such as alkali salts of ethylene-diamine-tetraacetic acid, and filled into injection phials or ampoules.

The capsules that contain one or more active ingredients or combinations of ingredients can, for example, be prepared by mixing the active ingredients with inert carriers such as lactose or sorbitol and encapsulating in gelatine capsules.

Suitable plugs can be prepared, for example, by mixing with specially prepared carriers, such as neutral fats or polyethylene glycol, or derivatives thereof.

A therapeutically effective daily adult dose is between 1 and 800 mg, preferably 10–300 mg.

The following examples illustrate the present invention without, however, thereby restricting its scope.

Examples of Pharmaceutical Formulations

| A) Tablets | per Tablet |
|---|---|
| Active ingredient | 100 mg |
| Lactose | 140 mg |
| Maize starch | 240 mg |
| Polyvinyl pyrrolidone | 15 mg |
| Magnesium stearate | 5 mg |
| | 500 mg |

The finely ground active ingredient, the lactose and a part of the maize starch are mixed together. The mixture is sieved, then moistened with a solution of polyvinyl pyrrolidone in water, kneaded, moist-granulated and dried. The granulate, the remaining maize starch and the magnesiuym stearate are sieved and mixed together. The mixture is then pressed into a suitable form and size of tablet.

| B) Tablet | per Tablet |
|---|---|
| Active ingredient | 80 mg |
| Maize starch | 190 mg |
| Lactose | 55 mg |
| Micro-crystalline cellulose | 35 mg |
| Polyvinyl pyrrolidone | 15 mg |
| Sodium carboxymethyl starch | 23 mg |
| Magnesium stearate | 2 mg |
| | 400 mg |

The finely ground active ingredient, a part of the maize starch, the lactose, the micro-crystalline cellulose and the polyvinyl pyrrolidone are mixed together, the mixture is sieved and worked with the remaining part of the maize starch and water into a granulate, which is dried and sieved. The sodium carboxymethyl starch and the magnesium stearate are added and the mixture is pressed into tablets of a suitable size.

| C) Pills | Per Pill |
|---|---|
| Active ingredient | 5 mg |
| Maize starch | 41.5 mg |
| Lactose | 30 mg |
| Polyvinyl pyrrolidone | 3 mg |
| Magnesium stearate | 0.5 mg |
| | 80 mg |

The active ingredient, the maize starch, the lactose and the polyvinyl pyrrolidone are well mixed together and moistened with water. The moist mass is pressed through a sieve having a 1 mm mesh size, dried at 45° C. and the granulate is then mashed through the same sieve. After adding and mixing the magnesium stearate, it is pressed in a tabletting machine into dished pills having a diameter of 6 mm. The pills obtained are then coated by a known method with a layer that substantially comprises sugar and talc. The finished pills are polished with wax.

| D) Capsules | per Capsule |
|---|---|
| Active ingredient | 50 mg |
| Maize starch | 268.5 mg |
| Magnesium stearate | 1.5 mg |
| | 320 mg |

The substance and the maize starch are mixed together and moistened with water. The moist mass is sieved and dried. The dried granulate is sieved and mixed with the magnesium stearate. The final mixture is filled into hard-gelatine capsules, size 1.

| E) Ampoulle Solution | |
|---|---|
| Active ingredient | 50 mg |
| Sodium chloride | 50 mg |
| Aqua pro inj. | 5 ml |

The active ingredient is dissolved in water at its own pH or, if desired, at a pH between 5.5 and 6.5, and treated with isotonic sodium chloride. The solution obtained is filtered pyrogen-free and the filtrate is filled under aseptic conditions into ampoules that are then sterilized and heat sealed. The ampoules contain 5 mg, 25 mg and 50 mg of active ingredient.

| (F) Suppositories | |
|---|---|
| Active ingredient | 50 mg |
| Adeps solidus | 1650 mg |
| | 1700 mg |

The hard fat is melted. The milled active ingredient mixture is dispersed to a homogeneous mass at 40° C. It is cooled to 38° C. and moulded into slightly cooled suppository shapes.

We claim:
1. A compound of the formula (I):

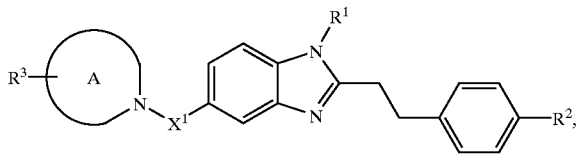

wherein:
$R^1$ represents $C_1$–$C_{10}$-alkyl or $C_3$–$C_6$-cycloalkyl, each optionally substituted once, twice or three times by any one or more of the following groups: $C_1$–$C_4$-alkoxy, phenoxy, hydroxyphenoxy, $C_1$–$C_4$-alkoxy-phenoxy, $C_3$–$C_6$-cycloalkyl, —$NH_2$, —NH($C_1$–$C_4$-alkyl), —N($C_1$–$C_4$-alkyl)$_2$, —NH—CO—($C_1$–$C_4$-alkyl), —CO—$NH_2$, —CO—NH—($C_1$–$C_4$-alkyl) or —NH—CO-benzyl, or represents phenyl-$C_1$–$C_4$-alkyl, in which the phenyl ring may be optionally substituted once, twice or three times by any one or more of the following radicals: $C_1$–$C_4$-alkyl, $CF_3$, fluorine, chlorine, bromine, COOH or COO—$C_1$–$C_4$-alkyl, $R_2$ is —C(=NH)$NH_2$ or —$CH_2$–$NH_2$;

$X^1$ is —CO—;

A together with the adjacent nitrogen forms a piperidine or piperazine ring;

$R^3$ represents a radical selected from the groups (a), (b) and (c):

(a) is —$NR^4R^5$;

·in which $R^4$ is hydrogen or a radical of the formula:

B-$(CH_2)_r$—$X^2$— wherein:
B represents a $C_1$–$C_6$-alkyl, $C_1$–$C_6$-haloalkyl, $C_2$–$C_6$-alkenyl, $C_2$–$C_6$-alkinyl, $C_1$–$C_6$-alkoxy-$C_1$–$C_6$-alkyl, $C_3$–$C_8$-cycloalkyl, phenyl, naphthyl, in which the phenyl, naphthyl group can be substituted by any one or more groups selected from halogen, nitro, cyano, $C_1$–$C_4$-alkyl, $C_1$–$C_4$-alkoxy, $C_1$–$C_4$-alkylthio, $C_1$–$C_4$-alkyl-$SO_2$—, $C_1$–$C_4$-alkyl-$PO_2$—O—, $C_1$–$C_5$-alkanoyl, $C_1$–$C_4$-alkoxycarbonyl, $C_1$–$C_4$-haloalkyl, $C_1$–$C_4$-haloalkoxy, $C_1$–$C_4$-haloalkylthio, $C_1$–$C_4$-cyanoalkyl, $C_1$–$C_4$-hydroxyalkyl, $C_1$–$C_4$-alkoxy-$C_1$–$C_4$-alkyl, carboxy, amino, $C_1$–$C_4$-alkylamino, di-($C_1$–$C_4$-alkyl)-amino, aminosulfonyl, phenyl and hydroxy, or B represents a phenyl group in which two adjacent carbon atoms are jointly substituted by a $C_1$–$C_4$-alkylenedioxy;

$X^2$ represents CO, NH—CO, $SO_2$, NH—$SO_2$, or a single bond, and r is 0 or a whole number from 1 to 4, $R^5$ represents hydrogen or a radical of the formula D—$(CH_2)_r$—, in which
D represents $C_1$–$C_6$-alkyl, $C_1$–$C_6$-haloalkyl, $C_2$–$C_6$-alkenyl, $C_2$–$C_6$-alkynyl, $C_1$–$C_6$-alkoxy-$C_1$–$C_6$-alkyl, $C_3$–$C_8$-cycloalkyl, phenyl, naphthyl, in which each phenyl, naphthyl group can be substituted by any one or more of the groups selected from: halogen, nitro, cyano, $C_1$–$C_4$-alkyl, $C_1$–$C_4$-alkoxy, $C_1$–$C_4$-alkylthio, $C_1$–$C_4$-alkyl-$SO_2$—, $C_1$–$C_4$-alkyl-$PO_2$—O—, $C_1$–$C_5$-alkanoyl, $C_1$–$C_4$-alkoxycarbonyl, $C_1$–$C_4$-haloalkyl, $C_1$–$C_4$-haloalkoxy, $C_1$–$C_4$-haloalkylthio, $C_1$–$C_4$-cyanoalkyl, $C_1$–$C_4$-hydroxyalkyl, $C_1$–$C_4$-alkoxy-$C_1$–$C_4$-alkyl, carboxy, amino, $C_1$–$C_4$-alkylamino, di-($C_1$–$C_4$-alkyl)-amino, aminosulphonyl, phenyl and hydroxy, or D represents a phenyl group, in which two adjacent carbon atoms are jointly substituted by $C_1$–$C_4$-alkylenedioxy; and t is 0 or a whole number from 1 to 4;

(b) is —E-phenyl,
in which
E stands for —$CH_2CH_2$— or —CH=CH—;

(c) is phenyl, which is substituted by any one or more substituents selected from halogen, trifluoromethyl and nitro;

or a tautomer, racemate, enantiomer, diastereoisomer or mixture thereof, or a pharmacologically unobjectionable acid-addition salt thereof.

2. A compound of the formula (I) as claimed in claim 1, wherein:

$R^3$ represents a radical of group (a), in which $R^4$ is as defined in claim 1, and $R^5$ is hydrogen or D—$(CH_2)_t$—, in which D represents $C_1$–$C_4$-alkyl, $C_3$–$C_6$-cycloalkyl, phenyl, naphthyl, in which the phenyl group can be optionally substituted by any one, two or three groups selected from halogen, $C_1$–$C_4$-alkyl-$SO_2$—, $C_1$–$C_4$-haloalkyl, $C_1$–$C_4$-haloalkoxy, aminosulphonyl, phenyl and hydroxy, and t is 0 if D is a $C_1$–$C_4$-alkyl group, or t is 1 or 2, if D is other than a $C_1$–$C_4$-alkyl group.

3. A compound of the formula (I) as claimed in claim 1, wherein $R^1$ represents $C_1$–$C_{10}$-alkyl or $C_3$–$C_6$-cycloalkyl, which can be optionally substituted once, twice or three times by any one or more of the following groups: $C_1$–$C_4$-alkoxy, phenoxy-, $C_1$–$C_4$-alkoxy-phenoxy, hydroxyphenoxy, $C_3$–$C_6$-cycloalkyl, —$NH_2$, —NH($C_1$–$C_4$-alkyl), —N($C_1$–$C_4$-alkyl)$_2$, —NH—CO—($C_1$–$C_4$-alkyl), —CO—$NH_2$, —CO—NH—($C_1$–$C_4$-alkyl) or —NH—CO-benzyl, or represents phenyl-$C_1$–$C_4$-alkyl, in which the phenyl ring can be optionally substituted by any one or more of the following radicals: $C_1$–$C_4$-alkyl, $CF_3$, fluorine, chlorine, bromine, COOH or COO—$C_1$–$C_4$-alkyl, or $R^2$ represents —C(=NH)$NH_2$ or —$CH_2$—$NH_2$;

A represents piperidine or piperazine;

$R^3$ represents a radical selected from the group (a), (b) and (c):

(a) —$NR^4R^5$;
in which
$R^4$ stands for B—$X^2$— in which

B is $C_1$–$C_6$-alkyl, phenyl, naphthyl or dihydrobenzo[1,4] dioxinyl, whereby each phenyl, naphthyl, benzo group can be substituted by one or more groups selected from: halogen, cyano, $C_1$–$C_4$-alkyl, $C_1$–$C_4$-alkoxy, $C_1$–$C_4$-alkyl-$SO_2$—, $C_1$–$C_4$-alkyl-$PO_2$—O—, $C_1$–$C_4$-alkanoyl, $C_1$–$C_4$-alkoxycarbonyl, $C_1$–$C_4$-haloalkyl, $C_1$–$C_4$-haloalkoxy, phenyl, amino, $C_1$–$C_4$-alkylamino, di-($C_1$–$C_4$-alkyl)-amino, aminosulfonyl, carboxy and hydroxy;

$X^2$ represents —CO—, —NH—CO— or a single bond, $R^5$ represents hydrogen or methyl, (b)-E-phenyl,
in which
E is —$CH_2CH_2$— or —CH=CH—;

(c) phenyl substituted by any one or two substituents selected from: fluorine, chlorine, trifluoromethyl and nitro;

or a tautomer, racemate, enantiomer, diastereoisomer or mixture thereof, or a pharmacologically unobjectionable acid-addition salt thereof.

4. A compound of the formula (I), as claimed in claim 1, wherein:

$R^1$ represents an unsubstituted $C_1$–$C_{10}$-alkyl or $C_3$–$C_6$-cycloalkyl group, or a $C_1$–$C_4$-alkyl group that is substituted once or twice by $C_1$–$C_4$-alkoxy, phenoxy-, $C_1$–$C_4$-alkoxy-phenoxy, hydroxyphenoxy, $C_3$–$C_6$-cycloalkyl, —$NH_2$, —NH($C_1$–$C_4$-alkyl), —N($C_1$–$C_4$-alkyl)$_2$, —NH—CO—($C_1$–$C_4$-alkyl), —CO—$NH_2$, —CO—NH—($C_1$–$C_4$-alkyl) or —NH—CO-benzyl, or represents phenyl-$C_1$–$C_3$-alkyl, in which the phenyl ring is optionally substituted once or twice by $C_1$–$C_4$-alkyl, $CF_3$, fluorine, chlorine, bromine, COOH or COO—$C_1$–$C_4$-Alkyl, $R^2$ represents —C(=NH)$NH_2$ or —$CH_2$—$NH_2$;

A represents piperidine-1,4-diyl or piperazine-1,4-diyl;

$R^3$ represents a radical selected from the group (a), (b) and (c):

(a) is —$NR^4R^5$;
in which
$R^4$ represents $C_1$–$C_6$-alkylaminocarbonyl, phenylcarbonyl, phenylaminocarbonyl or dihydrobenzo[1,4]dioxinylcarbonyl, in which each phenyl, benzo group can be substituted once or twice by halogen, $C_1$–$C_4$-alkyl, $C_1$–$C_4$-alkoxy, $C_1$–$C_4$-alkanoyl, $C_1$–$C_4$-alkoxycarbonyl, $C_1$–$C_4$-haloalkyl, $C_1$–$C_4$-haloalkoxy, carboxy or hydroxy;

$R^5$ represents hydrogen or methyl;

(b) is —E-Phenyl,
in which
E represents —$CH_2CH_2$— or —CH=CH—;

(c) is phenyl substituted by one or two substituents selected from fluorine, chlorine, trifluoromethyl and nitro;

or a tautomer, racemate, enantiomer, diastereoisomer or mixture thereof, or a pharmacologically unobjectionable acid-addition salt thereof.

5. A compound of the formula (I) as claimed in claim 1, wherein:

$R^1$ represents unsubstituted $C_1$–$C_{10}$-alkyl, $C_3$–$C_6$-cycloalkyl or $C_1$–$C_4$-alkyl that is substituted by $C_1$–$C_4$-alkoxy, phenoxy, $C_1$–$C_4$-alkoxy-phenoxy, hydroxyphenoxy, $C_3$–$C_6$-cycloalkyl, —$NH_2$, —NH($C_1$–$C_4$-alkyl), —N($C_1$–$C_4$-alkyl)$_2$, —NH—CO—($C_1$–$C_4$-alkyl), —CO—$NH_2$, —CO—NH-($C_1$–$C_4$-alkyl) or —NH—CO-benzyl, or phenyl-$C_1$–$C_3$-alkyl, in which the phenyl ring can be substituted by $C_1$–$C_4$-alkyl, $CF_3$, fluorine, chlorine, bromine, COOH or COO—$C_1$–$C_4$-alkyl.

6. A compound of the formula (I) as claimed in the claim 1, wherein:

R¹ represents methyl, ethyl, propyl, butyl, pentyl, hexyl, heptyl, octyl, nonyl, decyl, cyclopropyl, cyclopentyl or cyclohexyl, or
a methyl, ethyl or propyl radical, each substituted by methoxy, ethoxy, cyclopropyl, cyclopentyl, cyclohexyl, phenyl, methoxyphenoxy, —NH$_2$, —NH(C$_1$–C$_4$-alkyl), —N(C$_1$–C$_4$-alkyl)$_2$, —NH—CO-methyl, —CO—NH$_2$, —CO—NH-methyl or —NH—CO-benzyl, or R¹ represents benzyl that is once or twice substituted by methyl, ethyl, propyl, CF$_3$, fluorine, chlorine, bromine, COOH, COOMe or COOEt, or R¹ represents phenylethyl that is once or twice substituted by methyl, ethyl, propyl, CF$_3$, fluorine, chlorine, bromine, COOH, COOMe or COOEt.

7. A compound of the formula (I) as claimed in claim 1, wherein:
R¹ represents methyl, ethyl, propyl, pentyl, n-decyl, cyclopropyl or cyclohexyl, or a methyl, ethyl or propyl radical, each substituted by methoxy, ethoxy, cyclopropyl, cyclopentyl, cyclohexyl, phenyl or methoxyphenoxy, or R¹ represents benzyl substituted once or twice by methyl, CF$_3$, COOH, COOMe or COOEt.

8. A compound of the formula (I) as claimed in claim 1, wherein:
R¹ is methyl, ethyl, propyl, pentyl, cyclopropyl, phenylethyl, phenylpropyl, cyclopropylmethyl, or benzyl that is once or twice substituted by CF$_3$, COOH, COOMe or COOEt.

9. A compound of the formula (I) as claimed in claim 1, wherein:
R¹ is methyl or cyclopropyl.

10. A compound of the formula (I) as claimed in claim 1, wherein:
R¹ is methyl or cyclopropyl; and
R² is —C(=NH)NH$_2$.

11. A compound according to claim 1 having the formula (IA):

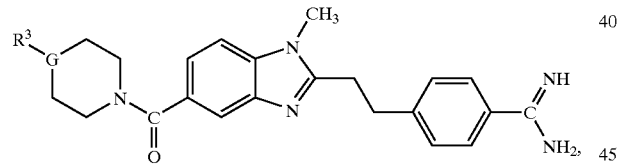

(IA)

wherein R³ is as defined in claim 1, and
G is CH or N.

12. A compound of the formula I according to claim 1 selected from the following compounds:
[2-(4-amidinophenyl)-ethyl]-1-methyl-benzimidazole-5-yl-carboxylic acid-[4-(3-phenyl-allyl)-piperazinyl]-amid-dihydrochloride;
[2-(4-amidinophenyl)-ethyl]-1-methyl-benzimidazole-5-yl-carboxylic acid-[4-(2-nitro-4-trifluoromethyl-phenyl)-piperazinyl]-amide-dihydrochloride;
[2-(4-amidinophenyl)-ethyl]-1-methyl-benzimidazole-5-yl-carboxylic acid-[(2-cyclohexyl-ethyl)-piperazinyl]-amide-dihydrochloride;
[2-(4-amidinophenyl)-ethyl]-1-methyl-benzimidazole-5-yl-carboxylic acid-{4-[2-benzoylamino-(2,3-dihydro-benzo[1,4]dioxine)]-piperidinyl}-amide-hydrochloride;
[2-(4-amidinophenyl)-ethyl]-1-methyl-benzimidazole-5-yl-carboxylic acid-[4-(2,4-dioxo-1-oxa-3-aza-spiro[4,4]non-3-yl)-piperidinyl]-amide-hydrochloride;
[2-(4-amidinophenyl)-ethyl]-1-methyl-benzimidazole-5-yl-carboxylic acid-[4-(4-fluorobenzamido)-piperazinyl]-amide-hydrochloride;
[2-(4-amidinophenyl)-ethyl]-1-methyl-benzimidazole-5-yl-carboxylic acid-[4-(4-nitrophenyl)-piperazinyl]-amide-dihydrochloride;
[2-(4-amidinophenyl)-ethyl]-1-methyl-benzimidazole-5-yl-carboxylic acid-[4-(3-butyl-ureido)-piperidinyl]-amide-hydrochloride;
[2-(4-amidinophenyl)-ethyl]-1-methyl-benzimidazole-5-yl-carboxylic acid-(4-benzamidopiperidinyl)-amide-hydrochloride;
[2-(4-amidinophenyl)-ethyl]-1-methyl-benzimidazole-5-yl-carboxylic acid-{4-(3-(2,3-dichloro-phenyl)-ureido]-piperidinyl}-amide-hydrochloride;
2-(2-(4-aminomethylphenyl)-ethyl]-1-methyl-benzimidazole-5-yl-carboxylic acid-(4-benzamidopiperidinyl)-amide;
2-[2-(4-amidinophenyl)-ethyl]-1-(3-ethoxy-propyl)-benzimidazole-5-yl-carboxylic acid-(4-phenethyl-piperazinyl)-amide-dihydrochloride;
2-[2-(4-amidinophenyl)-ethyl]-1-(3-ethoxy-propyl)-benzimidazole-5-yl-carboxylic acid-(4-benzamidopiperidinyl)-amide-hydrochloride;
2-[2-(4-amidinophenyl)-ethyl]-1-(3-ethoxy-propyl)-benzimidazole-5-yl-carboxylic acid-[4-(3-phenyl-allyl)-piperazinyl]-amide-hydrochloride;
2[2-(4-amidinophenyl)-ethyl]-1-(3-ethoxy-propyl)-benzimidazole-5-yl-carboxylic acid-[4-(3-phenyl-allyl)-piperazinyl]-amide-trihydrochloride;
2-[2-(4-amidinophenyl)-ethyl]-1-(3-ethoxy-propyl)-benzimidazole-5-yl-carboxylic acid-[4-(3-phenyl-ureido)-piperidinyl]-amide-dihydrochloride;
2-[2-(4-aminophenyl)-ethyl[-1-(3-ethoxy-propyl)-benzimidazole-5-yl-carboxylic acid-{4-[2-benzoylamino-(2,3-dihydro-benzo[1,4]dioxin)]-piperydinyl}-amide-dihydrochloride;
2-[2-(4-amidinophenyl)-ethyl]-1-(3-ethoxy-propyl)-benzimidazole-5-yl-carboxylic acid-[(2-cyclohexyl-ethyl)-piperazinyl]-amide-trihydrochloride;
2-[2-(4-amidinophenyl)-ethyl]-1-methyl-benzimidazole-5-yl-carboxylic acid-[4-(3-chloro)-benzamidopiperidinyl]-amide;
2-[2-(4-amidinophenyl)-ethyl]-1-methyl-benzimidazole-5-yl-carbooxylic acid-[4-(3-brom)-benzamidopiperidinyl]-amide;
2-[2-(4-amidinophenyl)-ethyl]-1-methyl-benzimidazole-5-yl-carboxylic acid-[4-(2-hydroxy)-benzamidopiperidinyl]-amide;
2-[2-(4-amidinophenyl)-ethyl]-1-methyl-benzimidazole-5-yl-carboxylic acid-[4-(2-difluoromethylsulfanyl)-benzamidopiperidinyl]-amide;
2-[2-(4-amidinophenyl)-ethyl]-1-methyl-benzimidazole-5-yl-carbooxylic acid-[4-(3-difluoromethylsulfanyl)-benzamidopiperidinyl]-amide;
2-[2-(4-amidinophenyl)-ethyl]-1-methyl-benzimidazole-5-yl-carboxylic acid-[4-(2,3-dichloro)-benzamidopiperidinyl]-amide;
2-[2-(4-amidinophenyl)-ethyl]-1-methyl-benzimidazole-5-yl-carboxylic acid-[4-(2-methoxy)-benzamidopiperidinyl]-amide;
2-[2-(4-amidinophenyl)-ethyl]-1-methyl-benzimidazole-5-yl-carbooxylic acid-[4-(2-brom)-benzamidopiperidinyl]-amide;

2-[2-(4-amidinophenyl)-ethyl]-1-methyl-benzimidazole-5-yl-carboxylic acid-(4-(2-chloro)-benzamidopiperidinyl)-amide;

2[2-(4-amidinophenyl)-ethyl]-1-methyl-benzimidazole-5-yl-carboxylic acid-[4-(N-methyl) benzamidopiperidinyl]-amide;

2-[2-(4-amidinophenyl)-ethyl]-1-methyl-benzimidazole-5-yl-carboxylic acid-(4-anilinopiperidinyl)-amide;

2-[2-(4-amidinophenyl)-ethyl]-1-methyl-benzimidazole-5-yl-carboxylic acid-{4-[3-(2,3-dichloro)-phenyl-1-methyl-ureido]piperidinyl)-amide;

2-(2-(4-amidinophenyl)-ethyl]-1-methyl-benzimidazole-5-yl-carboxylic acid-[4-[3-(3-acetyl)-phenyl-ureido] piperidinyl amide;

2-[2-(4-amidinophenyl)-ethyl]-1-methyl-benzimidazole-5-yl-carboxylic acid-{4-[3-(3-carboxyl)-phenylureido] piperidinyl)-amide;

2-[2-(4-amidinophenyl)-ethyl]-1-methyl-benzimidazole-5-yl-carboxylic acid-{4-[3-(3methoxycarbonyl)-phenylureido]piperidinyl)-amide;

2-[2-(4-methoxycarbonylamidinophenyl)-ethyl]-1-methyl-benzimidazole-5-yl-carboxylic acid-{4-[3-(3-methoxycarbonyl)phenylureido]piperidinyl}-amide;

2-[2-(4-isobutoxycarbonylamidinophenyl)-ethyl]-1-methyl-benzimidazole-5-yl-carboxylic acid-{4-{3-(3-methoxycarbonyl)phenylureido]piperidinyl}-amide;

2-[2-(4-amidinophenyl)-ethyl]-1-methyl-benzimidazole-5-yl-carboxylicacid-{4-(3-(3-methylsulfanyl)phenylureido]piperidinyl}-amide;

2-[2-(4-amidinophenyl)-ethyl]-1-methyl-benzimidazole-5-yl-carboxylicacid-{4-[3-(3-iodo)-phenylureido]piperidinyl}-amide;

2-[2-(4-amidinophenyl)-ethyl]-1-methyl-benzimidazole-5-yl-carboxylic acid-{4-[3-(3-chloro)-phenylureido]piperidinyl}-amide; and 2-[2-(4-amidinophenyl)-ethyl]-1-methyl-benzimidazole-5-yl-carboxylic acid-{4-(3-(3-methoxycarbonyl)-phenyl-1-methyl-ureido]piperidinyl}-amide.

13. A method of treating bronchial asthma, allergic rhinitis, allergic conjunctivitis, atopical dermatitis, urticaria, allergic otitis, allergic stomach-intestinal illnesses, Morbus Crohn, colitis ulcerosa, anaphylactic shock, septic shock, shock-lung (ARDS), arthritis, chronic (obstructive) bronchitis, interstitial lung diseases, idiopathic lung fibrosis, fibrous alveolitis, sarcoidosis, histio-cytosis X, scar tissue formation, collagenoses, lupus eryhmetodis, sclerodermy, arteriosclerosis, psoriasis or neoplases in a patient, comprising adminstering to said patient an effective amount of a compound of formula (I) according to claim 1.

14. A pharmaceutical composition comprising a compound of formula (I) according to claim 1 and at least one pharmaceutically acceptable carrier.

* * * * *